US011583360B2

(12) United States Patent
Amanatullah et al.

(10) Patent No.: US 11,583,360 B2
(45) Date of Patent: Feb. 21, 2023

(54) METHOD FOR MONITORING OBJECT FLOW WITHIN A SURGICAL SPACE DURING A SURGERY

(71) Applicant: The Board of Trustees of the Leland Stanford Junior University, Stanford, CA (US)

(72) Inventors: Derek F. Amanatullah, Stanford, CA (US); Geoffrey Appelbloom, Stanford, CA (US); David Zhao, Stanford, CA (US); Rahim Nazerali, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 712 days.

(21) Appl. No.: 16/533,632

(22) Filed: Aug. 6, 2019

(65) Prior Publication Data

US 2020/0253683 A1 Aug. 13, 2020

Related U.S. Application Data

(60) Provisional application No. 62/715,119, filed on Aug. 6, 2018, provisional application No. 62/715,132, filed on Aug. 6, 2018.

(51) Int. Cl.
*A61B 90/00* (2016.01)
*G16H 40/20* (2018.01)
(Continued)

(52) U.S. Cl.
CPC .............. *A61B 90/06* (2016.02); *A61B 34/20* (2016.02); *A61B 34/25* (2016.02); *G06V 20/00* (2022.01);
(Continued)

(58) Field of Classification Search
CPC ......... A61B 90/06; A61B 34/20; A61B 34/25; A61B 2034/2057; A61B 2304/2065;
(Continued)

(56) References Cited

U.S. PATENT DOCUMENTS

2007/0093709 A1* 4/2007 Abernathie ............ A61B 90/39
600/407
2014/0081659 A1* 3/2014 Nawana ............... A61B 5/4833
705/3
(Continued)

*Primary Examiner* — Zade Coley
(74) *Attorney, Agent, or Firm* — Run8 Patent Group, LLC; Peter Miller

(57) ABSTRACT

One variation of a method for tracking objects within a surgical space during a surgery includes: based on a first image depicting the surgical space at a first time, detecting a first object and a constellation of objects in the surgical space, estimating distances from each object—in the constellation of objects—to the first object, and calculating a contamination risk of the first object based on contamination scores and distances to the first object for each object in the constellation of objects; calculating a contamination score of the first object based on a combination of the contamination risks of the first object during the surgery; and, in response to the contamination score of the first object exceeding a threshold contamination score prior to contact between the first object and a patient, serving a prompt within the surgical space to address sterility of the first object.

22 Claims, 5 Drawing Sheets

(51) Int. Cl.
*G16H 50/30* (2018.01)
*G16H 40/40* (2018.01)
*A61B 34/20* (2016.01)
*A61B 34/00* (2016.01)
*G06V 20/00* (2022.01)
*A61B 17/02* (2006.01)
*A61B 17/06* (2006.01)

(52) U.S. Cl.
CPC .............. *G16H 40/20* (2018.01); *G16H 40/40* (2018.01); *G16H 50/30* (2018.01); *A61B 17/02* (2013.01); *A61B 17/06114* (2013.01); *A61B 2034/2057* (2016.02); *A61B 2034/2065* (2016.02); *A61B 2034/254* (2016.02); *A61B 2090/061* (2016.02); *A61B 2505/05* (2013.01)

(58) Field of Classification Search
CPC ........ A61B 2034/254; A61B 2090/061; A61B 17/02; A61B 17/06114; A61B 2505/05; A61B 17/06; A61B 2090/081; A61B 2090/365; A61B 2090/371; A61B 50/33; A61B 2090/372; G16H 40/20; G16H 50/30; G16H 40/40; G16H 20/40; G06V 20/20; G06V 20/00; G06V 20/52; G06V 2201/034; G06K 9/00624
See application file for complete search history.

(56) References Cited

U.S. PATENT DOCUMENTS

2015/0305735 A1* 10/2015 Gorek .............. A61B 17/06061
606/147
2018/0197624 A1* 7/2018 Robaina ................ A61B 5/1176
2018/0247711 A1* 8/2018 Terry ..................... A61B 50/18
2020/0013024 A1* 1/2020 Armstrong ................ G06T 7/62

* cited by examiner

METHOD FOR MONITORING OBJECT FLOW WITHIN A SURGICAL SPACE DURING A SURGERY

CROSS-REFERENCE TO RELATED APPLICATIONS

This Application claims the benefit of U.S. Provisional Application No. 62/715,119, filed on 6 Aug. 2018, and U.S. Provisional Application No. 62/715,132, filed on 6 Aug. 2018, both of which are incorporated in their entireties by this reference.

TECHNICAL FIELD

This invention relates generally to the field of surgical guidance and more specifically to a new and useful method for tracking objects within a surgical space during a surgery in the field of surgical guidance.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method: Contamination

As shown in FIGS. 1, 2A, 2B, and 4, a method S100 for tracking objects within a surgical space during a surgery includes, based on a first image depicting the surgical space at a first time: detecting a first constellation of objects in the surgical space at the first time in Block S110; estimating distances from each object, in a first subset of objects in the first constellation of objects, to a first object in the first constellation of objects at the first time in Block S120; and calculating a first contamination risk of the first object based on contamination scores and distances to the first object for each object in the first subset of objects at the first time in Block S130. The method S100 also includes, based on a second image depicting the surgical space at a second time succeeding the first time: detecting a second constellation of objects in the surgical space at the second time in Block S110; estimating distances from each object, in a second subset of objects in the second constellation of objects, to the first object at the second time in Block S120; and calculating a second contamination risk of the first object based on contamination scores and distances to the first object for each object in the second subset of objects at the second time in Block S130. The method S100 further includes: calculating a first contamination score of the first object based on a combination of the first contamination risk and the second contamination risk in Block S132; and, in response to the first contamination score of the first object exceeding a threshold contamination score prior to contact between the first object and a patient occupying the surgical space, serving a prompt within the surgical space to address sterility of the first object in Block S134.

2. Method: Injury

Figure 1:
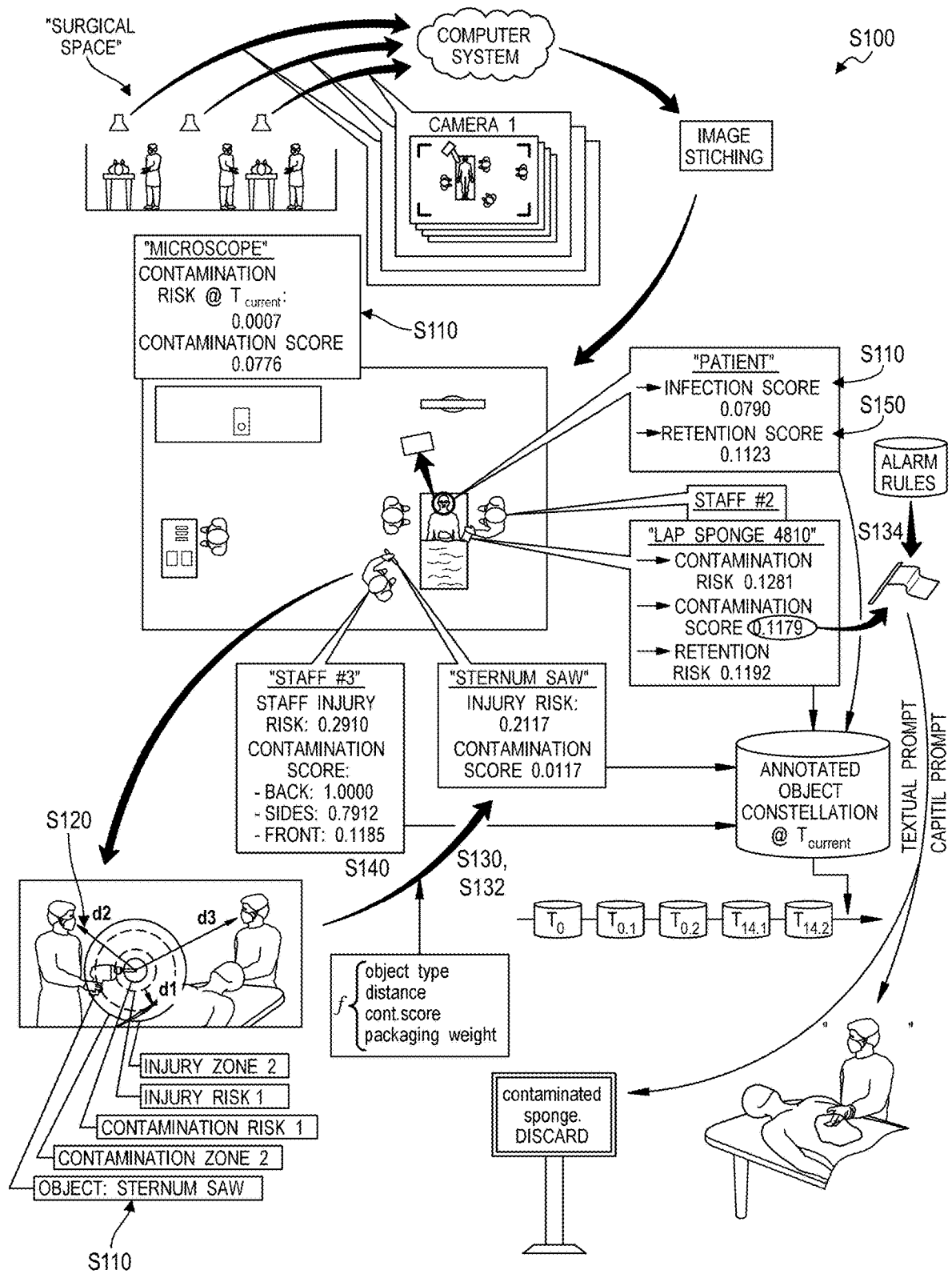
FIG. 1 is a flowchart representation of a method.
Figure 2A:
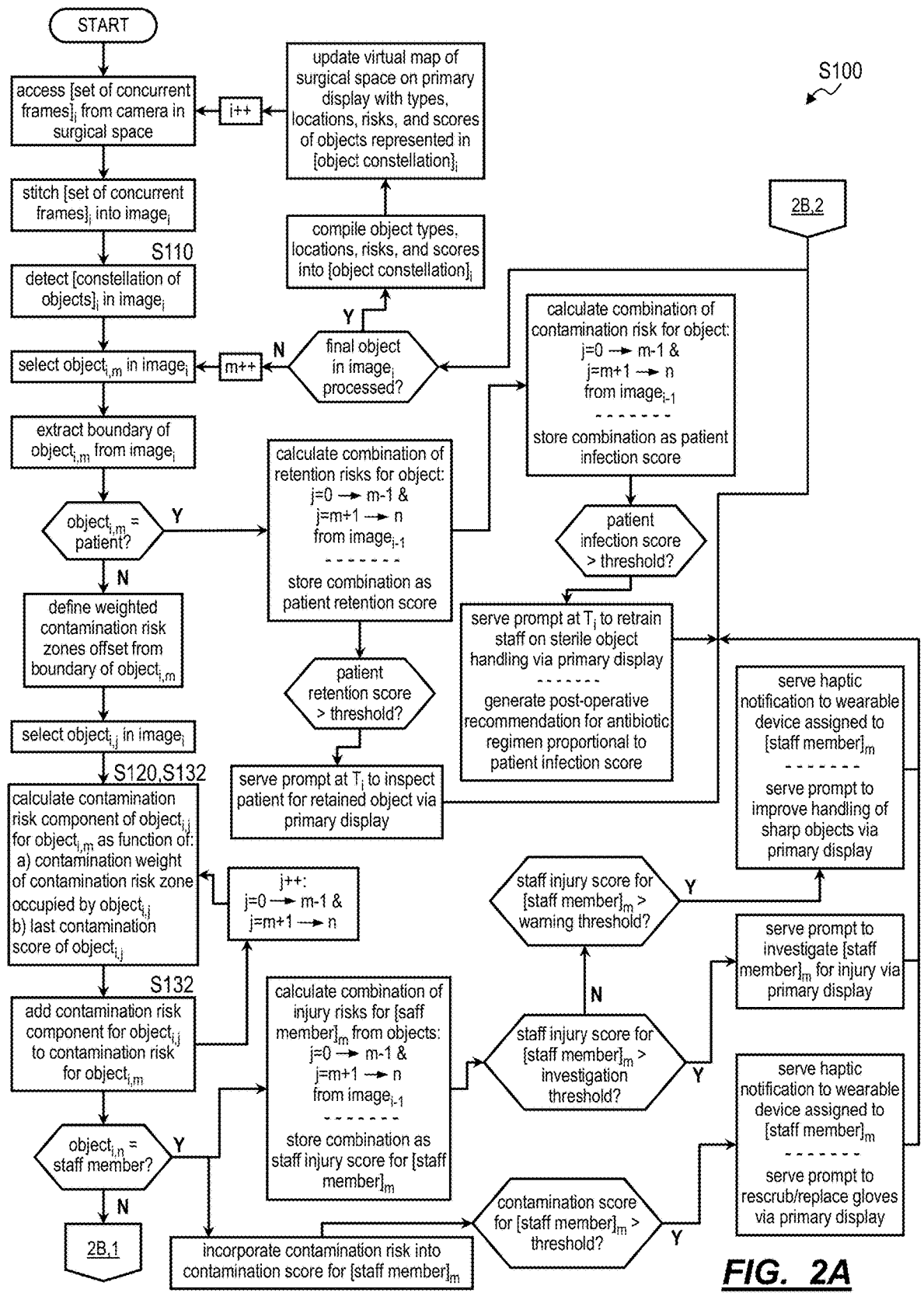
FIGS. 2A and 2B are a flowchart representation of one variation of the method.
Figure 2B:
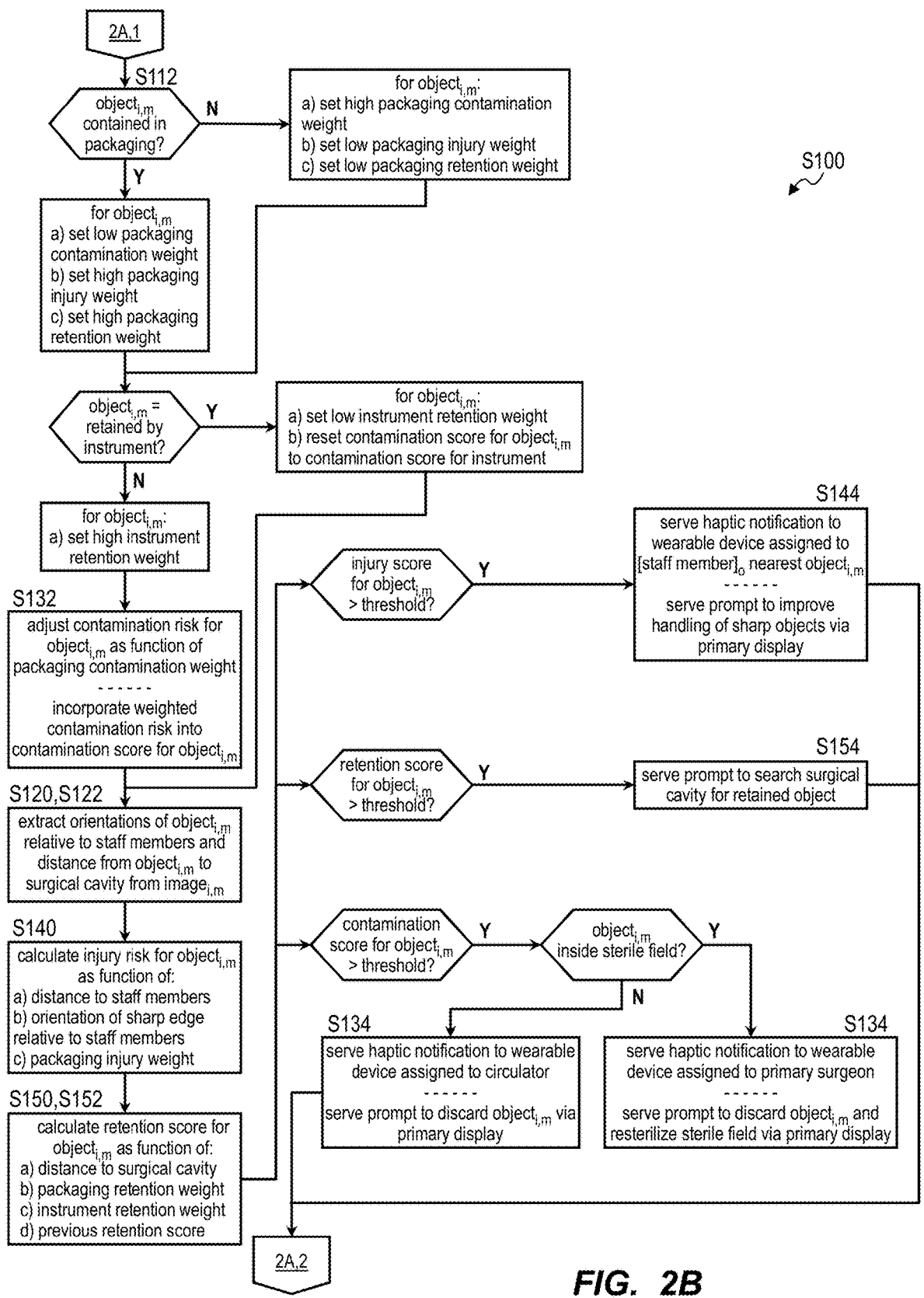

As shown in FIGS. 1, 2A, and 2B, one variation of the method S100 includes, based on a first image depicting the surgical space at a first time: detecting a first object and a set of surgical staff in the surgical space at the first time in Block S110; detecting a first packaging state of the first object at the first time in Block S112; estimating distances from each surgical staff member, in the set of surgical staff, to the first object at the first time in Block S120; and calculating a first injury risk of the first object based on the first packaging state of the first object and inversely proportional to distances to the first object for each surgical staff member in the set of surgical staff at the first time in Block S140. This variation of the method S100 also includes, based on a second image depicting the surgical space at a second time succeeding the first time: detecting the first object and the set of surgical staff in the surgical space at the second time in Block S110; detecting a second packaging state of the first object at the second time in Block S112; estimating distances from each surgical staff member, in the set of surgical staff, to the first object at the second time in Block S120; identifying a first surgical staff member, in the set of surgical staff, nearest the first object based on distances from each surgical staff member, in the set of surgical staff, to the first object at the second time in Block S122; and calculating a second injury risk of the first object based on the second packaging state of the first object and distances to the first object for each surgical staff member in the set of surgical staff at the second time in Block S140. This variation of the method S100 further includes, in response to the second injury risk exceeding the first injury risk and exceeding a threshold injury warning risk, directing a prompt to the first surgical staff member to address the second injury risk of the first object in Block S144.

3. Method: Retention

As shown in FIGS. 1, 2A, 2B, and 3, another variation of the method S100 includes, based on a first image depicting the surgical space at a first time: detecting a first object and a patient in the surgical space at the first time in Block S110; estimating a first distance from the first object to the patient at the first time in Block S120; and calculating a first retention risk of the first object inversely proportional to the first distance in Block S150. This variation of the method S100 also includes, based on a second image depicting the surgical space at a second time succeeding the first time: detecting the first object, the patient, a first surgical staff member proximal the first object, and a second surgical staff member proximal the first object in the surgical space at the second time in Block S110; estimating a second distance from the first object to the patient at the second time in Block S120; estimating a third distance from the first object to the first surgical staff member at the second time in Block S120; estimating a fourth distance from the first object to the second surgical staff member at the second time in Block S120; and calculating a second retention risk of the first object inversely proportional to the second distance in Block S150. This variation of the method S100 further includes: calculating a retention score of the first object based on a combination of retention risks of the first object over time during the surgery in Block S152; and, in response to the retention score of the first object exceeding a threshold retention score and, in response to the third distance exceeding the fourth distance, serving a prompt to the second surgical staff member to retrieve the first object from the patient in Block S154.

2. Applications

Generally, Blocks of the method S100 can be executed by a computer system (e.g., a local computing device, a computer network, a remote server): to detect and track objects in a live feed of images of a surgical space during a surgery; to interpret risk of contamination of each object based on its proximity to other objects in the surgical space and contamination states (or "contamination scores") of these other objects; to interpret risk of injury to surgical staff for select objects containing sharp or acute surfaces based on proximity to surgical staff in the surgical space and packaging states of these select objects; and/or to interpret retention risk to the patient for select (e.g., small) objects based on proximity to the patient and duration of contact with the patient. In particular, the computer system can detect and track a constellation of objects moving within the surgical space—including into and out of a sterile field—such as surgical textiles, gloves, surgical needles, tool drivers, retractors, cutting tools, scrubbed surgical staff, nonsterile surgical staff, and a patient moving relative to an operating table, a back table, a floor, and other fixed infrastructure in the surgical space. The computer system can then execute subsequent Blocks of the method S100 to selectively serve prompts to surgical staff in the surgical space to address specific objects that exhibit elevated risk of contamination (e.g., by discarding or sterilizing these objects), risk of injury to surgical staff (e.g., by repositioning these objects), and/or risk of being retained in the patient (e.g., by retrieving these objects).

In particular, probability that a particular object that entered the surgical space in a sterile condition is now contaminated may increase proportional to contamination of other objects in the surgical space (such as represented by contamination scores of these other objects) and inversely proportional to the particular object's distance to these other objects. Such probability of contamination by other objects in the surgical space may compound for the object throughout the duration of the surgery. The computer system can therefore: estimate contamination risk for a particular object within a time interval (e.g., 50 milliseconds) represented by one image of the surgical space based on distances between the particular object and other objects depicted in this image; repeat this process for each subsequent time interval represented by each subsequent images of the surgical space to reflect changes in contamination risk as other objects move relative to the particular object; and aggregate (or integrate, compile) these contamination risks for the particular object over time to calculate a "contamination score" representing a probability that the particular object has become contaminated since entering the surgical space in a sterile condition. The computer system can execute this process for each other object in the surgical space (e.g., for needles, needle drivers, surgical textiles, gloves) and/or for discrete regions of objects in the surgical space (e.g., torsos and arms of scrubbed surgical staff). The computer system can then: flag objects associated with contamination scores that exceed a threshold contamination score, such as defined by a hospital for all surgeries it hosts or by a primary surgeon performing the operation; and selectively serve prompts to surgical staff to discard, redress, or re-sterilize these flagged objects. For example, the computer system can serve such a prompt to a surgical staff member nearest a flagged object, to a circulating staff member tasked with handling contaminated objects, and/or to the primary surgeon through targeted haptic (e.g., vibratory) alerts at devices carried by these surgical staff paired with visual notifications rendered on a display mounted in the surgical space. The computer system can therefore execute Blocks of the method S100 to track and automatically trigger rapid responses to changes in sterility of objects in the surgical space before these objects contact the patient and/or before these objects enter the sterile field around the patient during the surgery.

Similarly, probability that a particular object defining a sharp or acute surface (e.g., a needle, a knife, a saw blade) will injure surgical staff in the surgical space may increase inversely proportional to the particular object's distance to these surgical staff and may be a function of whether the particular object is still contained in its packaging, how the particular object is retained, and the orientation of the particular object relative to these surgical staff. The computer system can therefore calculate near-instantaneous probability of injury to surgical staff by the particular object (i.e., an "injury risk") based on its current packaging state, retention, and orientation, as extracted from a current image of the surgical space. The computer system can then: flag the particular object if its current injury risk exceeds a threshold injury risk, such as assigned to a type of the particular object and defined by a hospital for all surgeries it hosts or by a primary surgeon performing the operation; and selectively serve a prompt to a particular surgical staff member currently handling the particular object to redress handling safety of the particular object, such as by serving a targeted haptic (e.g., vibratory) alert to a device assigned to the particular surgical staff member and rendering a corresponding visual notification on the display mounted in the surgical space. Following this prompt, the computer system can continue to calculate injury risks for this particular object based on features extracted from subsequent images of the surgical space and escalate this prompt to other surgical staff in the surgical space if the injury risk for the particular object continues to increase or does not drop below the threshold injury risk within a threshold period of time (e.g., ten seconds) following the initial prompt. The computer system can execute this process concurrently for each other (sharp) object in the surgical space. Furthermore, the computer system can: integrate injury risks of a particular object over time throughout the surgery to calculate an injury score that represents a measure of effective handling of the particular object by surgical staff throughout the surgery; and selectively prompt surgical staff to retrain on handling of the particular object or flag a type of the particular object as risky for surgical staff if the injury score for this particular object is high. The computer system can therefore execute Blocks of the method S100 to track and automatically trigger rapid, preemptive response to risky handling of objects that may lead to injury of surgical staff working in the surgical space.

Similarly, probability that a particular object will be retained (e.g., unintentionally left behind) in the patient upon completion of the surgery may increase inversely with distance between the particular object and the patient, may increase with time that the particular object is in contact with the patient (or the patient's wound specifically), and may be a function of whether or how the object particular is retained. The computer system can therefore calculate near-instantaneous risk of retention of the particular object in the patient (i.e., a "retention risk") based on its current distance from the patient and its current state of retention, as extracted from a current image of the surgical space. The computer system can also integrate retention risks of the particular object during the surgery to calculate a retention score of the particular object, which reflects a trajectory of the particular object relative to the patient, a duration of contact between the particular object and the patient, and therefore an aggregate probability that the particular object will be retained in the patient upon conclusion of the surgery. The computer system can then: flag the particular object if its current retention score exceeds a threshold retention score, such as assigned to a type of the particular object and defined by a hospital for all surgeries it hosts or by a primary surgeon performing the operation; and selectively serve a prompt to a particular surgical staff member current handling or nearest the particular object to retrieve the particular object from the patient. Following this prompt, the computer system can continue to track the location of the particular object relative to the patient and escalate this prompt to other surgical staff in the surgical space if the particular object is not removed or if the prompt is not silenced by a surgical staff member within a threshold period time (e.g., ten seconds) following the initial prompt. The computer system can execute this process concurrently for each other object in the surgical space throughout the surgery. The computer system can therefore execute Blocks of the method S100 to track, remind surgical staff of, and automatically trigger retrieval of objects exhibiting greatest probability of unintentional retention in the patient upon conclusion of the surgery.

The computer system can also: assemble these object location, orientation, packaging state, retention condition, contamination risk, injury risk, and/or retention risk data into timeseries path and condition data for objects moving through the surgical space during the surgery; present these data to surgical staff in real-time during the surgery to enable rapid, real-time (visual) access to object flow through the surgical space; and store these data as a record of the surgery. The computer system can then derive post-operative insights for the surgery based on these timeseries object data, such as: efficiency of the surgery; complexity of the surgery; and performance of the surgical staff. More specifically, the computer system can leverage inter-operative timeseries object path and condition data recorded during the surgery to derive objective insights relating to efficiency, complexity, and/or risk of the surgery.

Furthermore, the computer system can predict patient outcome following the surgery based on these timeseries object path and condition data, such as: patient recovery time as a function of quantity of objects consumed during the surgery; and/or risk of infection for the patient based on contamination risk of objects consumed over the duration of the surgery.

Therefore, the computer system can execute Blocks of the method S100 to: implement computer vision techniques to detect and track locations of individual objects within a surgical space throughout a surgery; leverage ontologies or contextual awareness of relationships between objects, surgical staff, and the patient to monitor contamination, injury, and/or retention risks for individual objects; and derive and present real-time inter-operative guidance for maintaining sterility within the sterile field, reducing object-related risks to surgical staff, and removing all unintentionally-retained objects from the patient during the surgery. The computer system can also execute Blocks of the method S100 to quantify the surgery, to predict and address an outcome of the surgery, and surface opportunities for increasing efficiency and reducing risk related to object flow within surgeries based on timeseries object data from one or many surgeries.

The method S100 is described herein as executed by the computer system to monitor and characterize object flow within a surgical space in (near) real-time. However, any other local or remote device or system can implement similar methods and techniques to monitor and characterize flow objects within a surgical space.

3. System

Generally, throughout the surgery, the computer system can access a stream of images recorded by a set of (i.e., one or more) cameras arranged in or facing the surgical space. For example, the computer system can also a stream of images from a camera that includes a color (e.g., RGB) camera, a 3D stereoscopic color camera, and/or a 2D or 3D depth sensor and can return 2D or 3D color images, depth maps, or point clouds (e.g., 3D color point clouds) to the computer system for processing on a regular interval, such as 30 Hz or 60 Hz.

In one implementation, the camera is fixed to a stand overhead an inventory table—offset from an operating table—in the surgical space such that images captured by the camera depict packaged and unpackaged objects in inventory in the surgical space. Alternatively, the camera can be mounted directly over or facing the operating table such that images captured by the camera depict objects handled by a surgeon, inserted into a patient, and withdrawn from the patient.

Yet alternatively, multiple cameras can be arranged in the surgical space within overlapping fields of view. For example, a first camera can be arranged over the inventory table, and a second camera can be arranged over the operating table and define a field of view that overlaps the field of view of the first camera, such as 10% overlap in area at a plane intersecting the floor of the surgical space. In a similar example, a set of cameras can be arranged throughout the surgical space, including: a first subset of cameras arranged at a first density (and/or defining a first imaging resolution) over high-risk zones in the surgical space (e.g., over an operating table to face a patient, a surgical cavity, and scrubbed surgical staff; over a sterile field); a second subset of cameras arranged at a second, lower density (and/or defining a second, lower imaging resolution) over medium-risk zones (e.g., over a traffic area between the operating table and the back table; around a periphery of the sterile field); and a third subset of cameras arranged at a third, even-lower density (and/or defining a third, even-lower imaging resolution) over low-risk zones (e.g., over a back table and a waste receptacle) in the surgical space.

In this implementation, the computer system can implement methods and techniques described below to individually process (approximately) concurrent images output by these cameras and can implement object tracking techniques to track objects moving from the field of view of one camera into the field of view of another camera during the surgery based on known positions of these cameras. Alternatively, the computer system can stitch process (approximately) concurrent images output by these cameras into composite images based on known positions of these cameras and then implement methods and techniques described below to process each composite image to track and characterize objects moving within the surgical space. For example, the computer system can: access a first set of color frames recorded by a set of color cameras arranged in the surgical space at approximately a first time; compile this first set of color frames into a first (composite) image defining a first 3D color point cloud represented the surgical space based on known locations of the set of color cameras; process this first 3D color point cloud according to methods and techniques described below to detect and characterize objects in the surgical space at the first time; and repeat this process for groups of concurrent images recorded by these cameras during subsequent time intervals (e.g., 50-millisecond time intervals) during the remainder of the surgery.

However, the computer system can access frames or images—recorded by one or more cameras or other optical sensors deployed in the surgical space—in any other format and at any other frequency during the surgery.

4. Object Detection and Tracking in Surgical Space

Block S110 of the method S100 recites, based on a first image depicting the surgical space at a first time, detecting a first constellation of objects in the surgical space at the first time. One variation of the method S100 further includes Block S112, which recites detecting a first packaging state of the first object at the first time. Generally, in Blocks S110 and S112, the computer system can implement computer vision techniques to detect, identify, and characterize objects depicted in an image of the surgical space recently recorded by the camera(s).

In one implementation, upon receipt of a next image from the camera (or upon generation of a next image from concurrent frames received from the set of cameras), the computer system scans the image for features representative of surgical tools (e.g., graspers, clamps, needle drivers, retractors, distractors, cutters, suction tips, microscopes), surgical drapes, consumables (e.g., lap sponges, needles, knife blades, saw blades), object packaging (e.g., needle trays, disposable packaging), disposal containers, surgical staff, and/or the patient. In particular, the computer system can: access a current image of the surgical space recorded during the surgery; implement computer vision techniques (e.g., template matching, a convolutional neural network) to detect fixed and movable objects in this image; and interpret locations of these objects in the surgical space from the image. For example, the computer system can estimate a lateral, longitudinal, and depth position of the centroid of the volume or area of an object detected in the current image relative to an origin defined in the surgical space.

The computer system then: stores locations of individual objects detected in the image in a 3D (or 2D) constellation of objects; and writes a timestamp from the image to this constellation of objects. For example, the computer system can represent the object constellation for objects detected in the current image in the form of a matrix or list of objects and lateral, longitudinal, and depth coordinates of visual spatial centroids of these objects in the current image relative to the origin of the surgical space.

The computer system can then annotate the current constellation of objects with types of these objects. In one example, the computer system: detects quick-response (or "QR) codes or barcodes applied to an inventory table, an operating table, surgical gloves, surgical gowns, surgical face masks, surgical instruments, surgical drapes, surgical sponges, surgical towels, etc. depicted in the image; queries a QR or bar code database to identify types of objects associated with these QR codes or barcodes; and populates the current object constellation with locations of these object types.

In another implementation, the computer system implements template matching, edge detection, and/or other computer vision techniques to identify objects detected in the image. For example, the computer system can access a database of template images of a corpus of objects commonly present in surgical spaces, such as various types of graspers, clamps, needle drivers, retractors, distractors, cutters, suction tips, microscopes, surgical textiles, drapes, surgical gowns, and gloves. In this example, the database of template images can include groups of images depicting object types in multiple orientations and/or in multiple states, such as: a first group of template images of a surgical needle in a loose state, a retained state (e.g., by a needle driver), a packaged in-tray state, and a sealed-packaged state; a second group of template images of a lap sponge in an unsealed folded state, an unsealed unfolded state, and a sealed-packaged state; a third group of template images of scissors in an open state and a closed state; a fourth group of template images of a knife in a blade-protected and blade-unprotected state; and fifth group of template images of a microscope in a draped state and an undraped state; etc. Each template image in this database can thus be labeled with an object type, object orientation, and object state represented by the template image. In this example, the computer system can: implement template matching techniques to match an object detected in the image to a representative object of this same type depicted in a template image in this template image database; interpret an orientation of the object in the surgical space based on alignment of the template image to the object in the image; and then transfer an object type label and a state label from the template image to a representation of this object in the current object constellation.

Additionally or alternatively, the computer system can implement object recognition techniques, deep learning, and/or artificial intelligence to identify types and states of objects directly from features extracted from the current image. The computer system can also confirm identification of an object based on proximity of another object, such as: proximity of a needle driver to confirm a needle detected in the image; proximity of a back table to confirm a sealed-packaged lap sponge; and proximity of a gloved hand to confirm a knife detected in the image.

In this implementation, the computer system can also implement hand, face, and body pose detection and extraction techniques to detect surgical staff in the surgical space. For example, the computer system can detect hands of surgical staff by: isolating blue and white regions in the image; implementing object recognition to identify each instance of a hand in a white surgical glove; and/or implementing object recognition to identify each instance of a blue sterile drape grasped by a hand in a white surgical glove. The computer system can also: implement face detection to detect faces of surgical staff and the patient in the image; detect bodies connected to these faces; identify a patient by presence over the operating table; identify a surgeon by proximity to the operating table and facing the patient; and identify an assistant, scrub tech, and circulator in the image based on their locations at greater distances from the operating table and/or at closer distances to a back table or inventory table.

The computer system can then annotate the current object constellation with object type, state, and/or orientation (or "pose") labels for each object detected in the image or for a subset of objects of interest detected in the image (e.g., surgical staff and dynamic objects that move within the surgical space).

The computer system can therefore generate an object constellation representing 3D (or 2D) locations of objects throughout the surgical space within a time interval (e.g., 50 milliseconds) represented by the current image of the surgical space. The computer system can repeat this process for each image recorded by the camera (or generated from frames received from the set of cameras) in the surgical space to generate an object constellation—annotated with object types, orientations, and/or poses of objects in the surgical space—for each of these images.

5. Object Tracking

The computer system can also implement object-tracking techniques to track objects over sequential images of the surgical space. In one implementation, the computer system: implements object-tracking techniques to track objects from preceding images to the current image (or from previous object constellations to the current object constellation); derives velocities of these objects based on their changes in position over these images (or over these object constellations); and annotates object representations in the current object constellation with velocities of the objects they connote.

Furthermore, by tracking objects from preceding images to the current image, the computer system can port last assessments of contamination, injury, and retention scores for objects in the surgical space into the current time interval. The computer system can then implement methods and techniques described below to reassess the contamination, injury, and retention risks of a particular object based on locations and scores of other objects in the surgical space and to update these contamination, injury, and retention scores for the object accordingly for the current time interval.

6. Contamination Risk

As shown in FIGS. 2A and 2B, Block S120 of the method S100 recites estimating distances from each object, in a first subset of objects in the first constellation of objects, to a first object in the first constellation of objects at the first time; and Block S130 of the method S100 recites calculating a first contamination risk of the first object based on contamination scores and distances to the first object for each object in the first subset of objects at the first time. Generally, in Blocks S120 and S130, the computer system can interpret a contamination risk (e.g., on a scale from "0.00000" to "1.00000") that a sterile object has been contaminated, such as based on a current state of the object, proximity of the object to other objects in the surgical space, and last contamination scores of these other objects. The computer system can then annotate a representation of this object in the current object constellation with its contamination risk and repeat this process for all objects or a subset of objects (e.g., dynamic objects) in the surgical space.

In particular, the computer system can implement a parametric, non-parametric, or statistical contamination risk model to estimate the risk that a sterile object is contaminated by another object in the surgical space during the current time interval as a function of proximity to other objects and surfaces in the surgical space and based on contamination scores of these other objects and surfaces. The computer system can then sum or integrate the contamination risk for the current time interval with past contamination risks for the object since the start of the surgery or since entry of the object into the surgical space in order to update a contamination score for the object. This contamination score may therefore: reflect a probability that the object has been contaminated since the start of the surgery or since entry of the object into the surgical space; and thus represent a probably that the patient develops an infection as a result of subsequent contact with object.

6.1 Object-Centric Contamination Risk Zones

In one implementation shown in FIGS. 1 and 2A, to calculate a contamination risk for a particular object detected in the current image, the computer system: defines a set of concentric "risk zone" rings or spherical shells centered around the particular object (e.g., in the current image or in the current object constellation); retrieves last contamination scores of objects located in these risk zones; calculates a sum of these contamination scores weighted by scalar factors associated with the risk zones that these other objects occupy around the particular object (and weighted by a packaging state of the particular object, orientations of these other objects, and/or sizes of these other objects, etc.); and stores this sum as a contamination risk of the particular object for the current time interval represented by the current image. More specifically, if a second object occupies a risk zone ring around the particular object, this second object may increase a risk that the particular object will be contaminated during the current time interval; the computer system can thus incorporate this risk into the contamination risk for the particular object for the current time interval.

For example, the computer system can define three risk zone rings around the particular object, each labeled with a "risk weight" scalar value. In this example, the computer system can define a "contact" zone at the surface of the particular object (and offset from the surface of the object by a distance corresponding to a resolution of the camera, such as two millimeters) and assigned a risk weight of "1.0". The computer system can also define: a "high contamination risk" zone in the immediate vicinity (e.g., within two centimeters) of the surface of the particular object and assigned a risk weight of "0.1"; a "moderate contamination risk" zone offset outwardly from the high contamination risk zone (e.g., by 20 centimeters) and assigned a risk weight of "0.01"; a "low contamination risk" zone offset outwardly from the moderate contamination risk zone (e.g., by one meter) and assigned a risk weight of "0.001"; and a "null contamination risk" zone beyond the low contamination risk zone and assigned a risk weight of "0.000". Therefore, the computer system can: detect a second object in the current image: calculate a product of the last contamination score of the second object and the risk weight of the contamination risk zone occupied by the second object (e.g., "0.1" if any surface of the second object falls within two centimeters of the surface of the particular object; "0.01" if a surface of the second object nearest the particular object falls between two centimeters and 20 centimeters from the surface of the particular object; "0.001" if a surface of the second object nearest the particular object falls between 20 centimeters and two meters from the surface of the particular object; or "0.000" if a surface of the second object nearest the particular object falls outside of one meter from the surface of the particular object); and store this product as a contribution of the second object to the current contamination risk of the particular object.

The computer system can repeat this process for each other object detected in the surgical space and sum risk contributions for each of these objects to calculate the contamination risk for the particular object for the current time interval.

In one example, the computer system detects a constellation of objects in the current image including: the particular object; a retractor; a surgical towel; a scrubbed surgical staff member; a nonsterile surgical staff member; and the patient. To calculate the contamination risk of the particular object for the current time interval, the computer system calculates: a first combination of a retractor contamination score of the retractor at approximately the current time (e.g., calculated upon conclusion of the preceding time interval corresponding to a preceding image of the surgical space)

and a first distance between the particular object and the retractor; a second combination of a towel contamination score of the surgical towel at approximately the current time and a second distance between the particular object and the surgical towel; a third combination of a scrubbed staff contamination score of the scrubbed surgical staff member at approximately the current time and a third distance between the particular object and the scrubbed surgical staff member; and a fourth combination of a nonsterile staff contamination score of the nonsterile surgical staff member at approximately the current time and a third distance between the particular object and the surgical staff member. The computer system then calculates a contamination risk for the current time interval based on a sum of the first combination, the second combination, the third combination, and the fourth combination. Later, the computer system can serve a prompt to address sterility of the particular object prior to a distance between the particular object and the patient falling below a threshold sterile field distance (e.g., one meter).

6.2 Object Size

In the foregoing implementation, the computer system can also weight a contribution of a second object to the contamination risk of the particular object based on a size of the second object. For example, a surgical staff member may represent a relatively large object in the surgical space; the larger surface area of the surgical staff member may therefore present greater opportunity to collect, retain, and culture bacteria and may therefore present greater risk of contaminating the particular object than a smaller object in the surgical space. Conversely, a small object—such as a needle—may define a small surface area that present less opportunity to collect, retain, and culture bacteria and thus less risk of contaminating the particular object than a larger object in the surgical space.

Therefore, the computer system can: extract a size (e.g., a width, a volume, a surface area) of a second object directly from the current image of the surgical space; and adjust the weight of contribution of the second object to the contamination risk of the particular object as a function of (e.g., proportional to) the size of the second object. Alternatively, the computer system can: retrieve a scalar size factor for the type of the second object (e.g., tagged to a template image matched to the second object); and adjust the weight of contribution of the second object to the contamination risk of the particular object according to this scalar size factor.

6.3 Object Orientation

In this implementation, the computer system can also weight a contribution of a second object to the contamination risk of the particular object based on an orientation of the second object relative to the particular object.

For example, the computer system can track contamination scores of the front of the torso, sides of the torso, the back of the torso, and gloves worn by of a scrubbed surgical staff member during the surgery. At the beginning of a surgery, the front of the torso and the gloves of a scrubbed surgical staff member may be predicted to be sterile; the computer system can therefore assign initial contamination scores of "0.000" to the front of the torso and the gloves of the surgical staff member. However, the sides and back of the surgical staff member's torso may be likely or known to be unsterile; the computer system can therefore assign initial contamination scores of "0.8" and "1.0" to the sides and back of the surgical staff member's torso, respectively, at the beginning of the surgery. During the surgery, the computer system can: track the orientation of these parts of the surgical staff member relative to the particular object; and weight the contribution of each of these parts of the surgical staff member to the contamination risk of the particular object based on its angular offset from the particular object.

Alternatively, the computer system can: calculate a surface area of each part of the surgical staff member directly in the field of view of (e.g., that directly faces, that is unobscured) the particular object; and then weight the contribution of each of these parts of the surgical staff member to the contamination risk of the particular object based on its surface area that directly faces the particular object.

6.4 Object Packaging

In this implementation, the computer system can also weight a contamination risk for the current time interval based on a packaging state of the particular object, as shown in FIG. 1. For example, for lap sponges sealed in packagings, the computer system can weight contamination risks for these objects by "null" value (or "0.0000") for the current time interval and thus preserve contamination scores of "null" (or "0.0000") for these objects. However, the computer system can implement the foregoing methods and techniques to separately calculate contamination risks and contamination scores for packaging containing lap sponges, etc.; once this packaging is opened, the computer system can implement the foregoing methods and techniques to calculate risk scores for lap sponges removed from this packaging based on proximity of the packaging to these lap sponges and the contamination score of the packaging (e.g., "1.0000").

In another example, the computer system detects and extracts a set of features in a first image—corresponding to a first time interval—received from the camera at a first time. Based on this set of features, the computer system identifies: a back table in the surgical space; a needle tray (i.e., "packaging") occupying the back table; a suture needle located occupying the needle tray; and a nonsterile region of a surgical staff member. The computer system then: calculates a product of a staff contamination score of the surgical staff member at approximately the first time and a distance from the needle tray to the nonsterile region of the surgical staff member; weights this product by a first packaging weight corresponding to presence of the suture needle in the needle tray; and stores this weighted product as a contamination risk of the suture needle for the first time interval. Later, upon receipt of a second image—corresponding to a second time interval—from the camera at a second time, the computer system can again detect a set of features in this second image. Based on this set of features, the computer system identifies: the suture needle; a needle driver; and the nonsterile region of the surgical staff member. The computer system can then: access a driver contamination score of the needle driver at approximately the second time; calculate a product of the staff contamination score of the nonsterile region of the surgical staff member at approximately the second time a distance from suture needle to the surgical staff member in the surgical space; and weight a combination of the driver contamination score and this product by a second weight—greater than the first weight—corresponding to removal of the suture needle from the needle tray. The computer system can then store this weighted combination as the second contamination risk of the suture needle for the second time interval.

6.5 Parametric Risk Function

Figure 4:
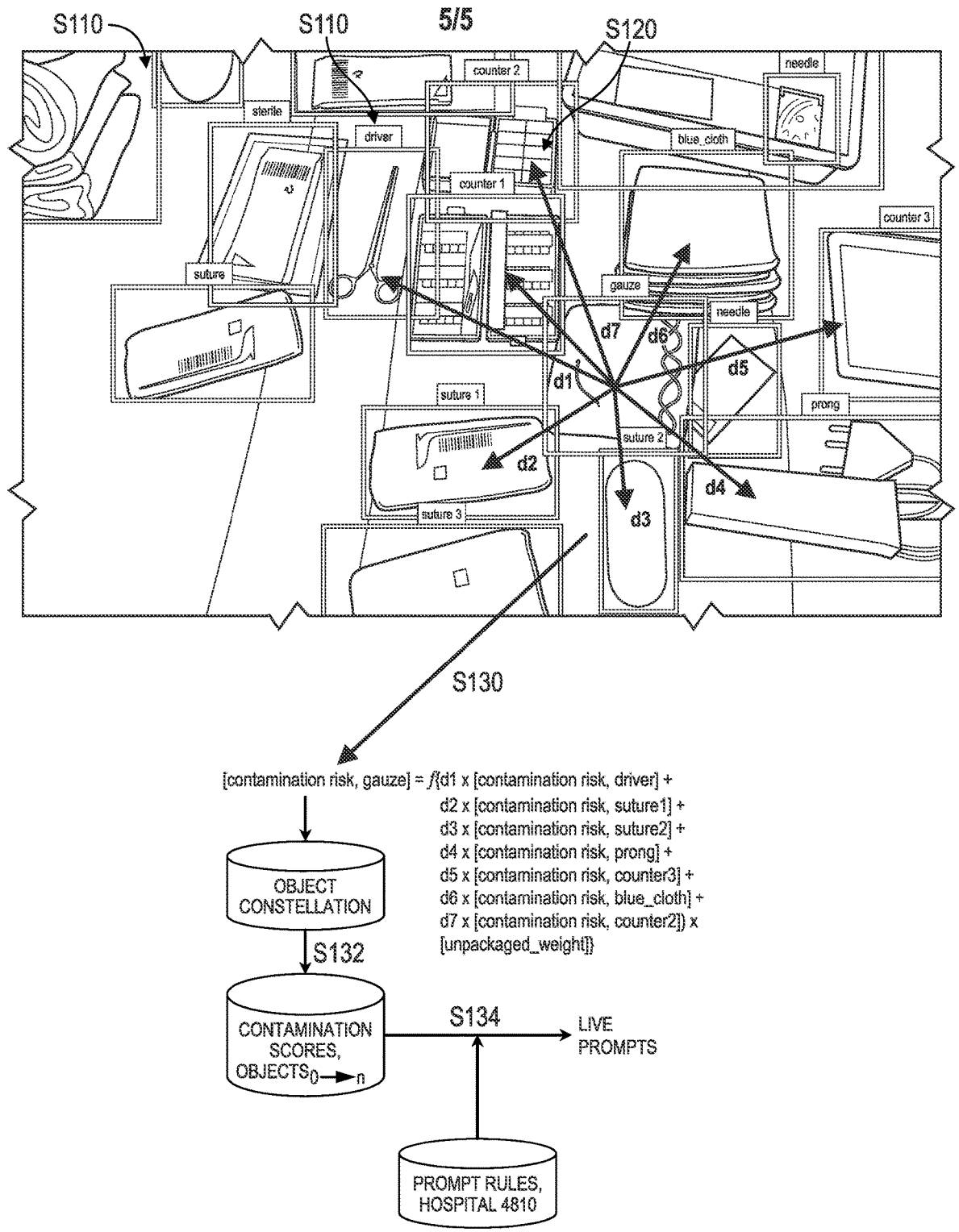
FIG. 4 is a flowchart representation of one variation of the method.

In one variation shown in FIG. 4, rather than define discrete risk zones with discrete risk weights per risk zone, the computer system can instead implement a parametric function (e.g., a logarithmic function) that outputs a risk that a second object will contaminate a particular object as a function of distance between the second object and the particular object (and as a function of size of the second object orientation of the second object, and/or packaging state of the particular object, etc.). The computer system can then implement this process for each other object detected in the current image and combines these risks that the particular object will be contaminated by these other objects into one contamination risk (e.g., from 0.00000 to 1.00000) for the current time interval.

However, the computer system can implement any other method or technique to calculate a contamination risk for a particular object in the surgical space based on features extracted from a current image of the surgical space. The computer system can then repeat this process for each other object or for select objects of interest in the surgical space.

6.6 Contamination Score

Block S132 of the method S100 recites calculating a contamination score of the first object based on a combination of the first contamination risk and the second contamination risk. Generally, in Block S132, the computer system can sum, integrate, or otherwise combine the contamination risks thus calculated for a particular object during the current and preceding time intervals into one numerical representation of the probability that the particular object is now contaminated (i.e., a "contamination score").

In one implementation, the computer system records initial contamination scores of "0.0000" for objects known as, predicted to be, or labeled as "sterile" upon initial entry into the surgical space (e.g., surgical instruments, suture needles, lap sponges). Similarly, the computer system records initial contamination scores of "1.0000" for objects known as, predicted to be, or labeled as "nonsterile" upon initial entry into the surgical space (e.g., the floor of the surgical space, backs of torsos of surgical staff). For a particular object with initial contamination score of "0.0000", the computer system can add contamination risks—calculated for this particular object based on features extracted from each image of the surgical space recorded after entry of the particular object into the surgical space and until the particular object is discarded or removed from the particular space—to this initial contamination score of "0.0000". The contamination score of the particular object may thus represent a history of proximity of the particular object to other objects—with their own contamination scores or that may be known to be contaminated—over the course of the surgery.

Furthermore, in the foregoing implementations, if any surface of a second object falls within a contact zone defined for the particular object (e.g., within two millimeters of the surface of the particular object) or is otherwise determined to have contacted the particular object, the computer system can automatically update the contamination scores of both the particular object and the second object to equal the greater of the contamination scores calculated for these objects for the current time interval.

For example, if the computer system detects that a particular object with a contamination score of "0.0097" is dropped on the floor of the space with contamination score of "1.0000", the computer system can update the contamination score of the particular object to "1.0000." In another example, if the computer system detects that a suture need with contamination score of "0.0013" makes contact with a needle driver with contamination score of "0.0140", the computer system can update the contamination score of the particular object to "1.0140." The computer system can therefore transfer a high contamination score from the second object to the particular object if these objects touch and if the current contamination score of the second object is currently greater than the current contamination score of the particular object; and vice versa.

6.7 Contamination Category

In one variation, the computer system converts a contamination score on a continuum for a particular object into a discrete contamination category of the particular object, such as: "definitively contaminated" for a contamination score greater than "0.9500"; "likely contaminated" for a contamination score between "0.4000" and "0.9500"; "at risk for contamination" for a contamination score between "0.0500" and "0.4000"; and "sterile" for a contamination score less than "0.0500".

However, the computer system can represent contamination risks and a contamination score of an object in any other way. Furthermore, the computer system can repeat the foregoing processes to calculate a new contamination risk and to update a contamination score for an object depicted in consecutive images captured during the surgery.

7. Variation: Patient Infection Score

In one variation shown in FIG. 2A, the computer system executes the foregoing methods and techniques to calculate a contamination risk for the patient based on distances between the patient (or a wound or surgical cavity in the patient more specifically) and other objects in the space and based on current contamination scores, orientations, and/or sizes, etc. of these other objects. The computer system can then aggregate contamination risks thus calculated for patient during the surgery into a "patient infection score" that represents probability that contaminants (e.g., bacteria) from another object in the surgical space reached the patient (or the patient's wound or surgical cavity more specifically) during the course of the surgery.

Therefore, the computer system can calculate a current contamination score of a particular object—other than the patient—that represents a current probability that the particular object is contaminated (i.e., not sterile). When this contamination score exceeds a threshold score, the computer system can prompt surgical staff to address this particular object, such as by: discarding the particular object; re-sterilizing the particular object; or draping the particular object within a sterile drape or towel. For example, the computer system can direct this prompt specifically to an individual surgical staff members member nearest the particular object, holding the particular object, or assigned responsibility for the particular object, such as by: directing a circulator staff member to retrieve a sponge from the floor; directing an assistant holding a suction wand with high contamination score to replace its suction head; or directing a surgeon reaching for a needle driver with high contamination score to elect a different needle driver.

Conversely, the computer system can implement similar methods and techniques to calculate and maintain a patient infection score for the patient, which may represent a probability that the patient will develop an infection as a result of contact with and/or proximity to other objects in the surgical space over the course of the surgery. The computer system can then selectively serve real-time or post-operative guidance to surgical space responsive to infection probability represented by this patient infection score. For example, when a patient infection score exceeds a low threshold score (e.g., "0.4000"), the computer system can prompt surgical staff to prescribe or adjust an antibiotic regimen for the patient upon conclusion of the surgery. However, when the patient infection score of the patient exceeds a high threshold score (e.g., "0.7000"), the computer system can serve a real-time prompt to surgical staff to pause the surgery and address sources of infection risk for the patient and flag the surgery for post-operative review.

8. Injury Risk

One variation of the method S100 shown in FIGS. 1, 2A, and 2B includes Block S140, which recites calculating a first injury risk of the first object based on the first packaging state of the first object and inversely proportional to distances to the first object for each surgical staff member in the set of surgical staff at the first time. Generally, in Block S140, the computer system can calculate a risk that a particular object injures a surgical staff member in the surgical space during the current time interval based on an orientation of the particular object, a packaging state of the particular object, and/or proximity of surgical staff in the surgical space to the particular object. In particular, the computer system can calculate injury risks of "sharp" objects and/or objects with "acute" surfaces—such as needles, knives, and blades—that represent possible sources of soft tissue injury to surgical staff in the surgical space.

In one implementation, the computer system implements methods and techniques similar to those described above to: detect a particular object—of a type known to include a sharp point, edge, or surface—in the current image; define injury risk zones around the particular object; detect a surgical staff member in the surgical space; detect a target region of the surgical staff member nearest the particular object; estimate a distance between the target region of the surgical staff member and the particular object; identify a particular injury risk zone around the particular object occupied by the target region of the surgical staff member; calculate a product (or other combination) of this distance and an injury risk weight for the particular injury risk zone; and store this product as an injury risk component for the particular object and the surgical staff member for the current time interval. The computer system can repeat this process for each other surgical staff member detected in the current image to calculate injury risk components for the particular object and these other surgical staff. The computer system can then sum these injury risk components to calculate an injury risk for the particular object for the current time interval.

However, the computer system can implement a parametric function, a table, a model, or a statistic in any other form or format to calculate an injury risk for the particular object for the current time interval.

8.1 Object Orientation

In this variation, the computer system can also weight an injury risk component for the particular object—representing a risk that the particular object injures a particular surgical staff member during the current time interval—based on an orientation of the particular object to the target region of the particular surgical staff member nearest the particular object, as shown in FIG. 2B. For example, the tip of a suture needle, the point and sharp edge of a knife blade, and a toothed edge of a saw blade may represent greatest risk of injury to surgical staff for these objects; whereas a needle driver retaining the suture needle, a spine and handle of the knife, and a spine and handle of the saw may represent little or no injury risk to surgical staff. Furthermore, such an object may represent greater injury risk to a surgical staff member if the sharp edge of the object is facing the surgical staff member than if this sharp edge is facing away from the surgical staff member.

Therefore, the computer system can: detect or interpolate a sharp or acute surface of the particular object; define injury risk zones around this sharp or acute surface specifically; and calculate a distance between a surgical staff member and this sharp or acute surface specifically. The computer system can then: cast a set of rays normal to a point of the particular object and/or from the sharp edge of the particular object; set an orientation weight for injury to the surgical staff member proportional to a quantity of these rays that intersect the target region of the surgical staff member; and then calculate an injury risk component for the particular object and this surgical staff member based on a combination of this distance, the injury risk zone occupied by the surgical staff member, and the orientation weight.

However, the computer system can implement any other method or technique to detect orientation of a sharp or acute surface of a particular object to a surgical staff member and can weight an injury risk component for this surgical staff member according to any other schema based on this orientation.

8.2 Packaging

Similarly, the computer system can weight an injury risk component for a surgical staff member according to a packaging state of the particular object, as shown in FIG. 2B. For example, a knife blade contained in a sleeve (i.e., "packaging"), a suture needle housed in a needle tray, and a cap suture needle may represent little or no injury risk to surgical staff; whereas an exposed knife blade, a loose or retainer suture needle, and an uncapped suture needle may represent greater injury risk to surgical staff. Therefore, the computer system can implement methods and techniques described above to detect the packaging state of a sharp object and to weight an injury risk component—for injury to a surgical staff member by the particular object—according to the packaging state of the particular object.

For example, the computer system can access a first image of the surgical space recorded at a first time and detect a first set of features in the first image. Based on the first set of features, the computer system can: detect the particular object (e.g., a suture needle, a knife blade)—including a sharp surface—in the surgical space; detect presence of a packaging (e.g., a needle tray, a blade sleeve) obstructing the sharp surface of the particular object; and identify a surgical staff member in the surgical space. The computer system can then calculate a first contamination risk of the particular object based: on a first contamination weight corresponding to presence of the packaging obstructing the sharp surface of the particular object; a staff contamination score of a first surface of the surgical staff member nearest and facing the particular object at approximately the first time; and a first distance from the particular object to the surgical staff member at approximately the first time. Concurrently, the computer system can calculate a first injury risk of the particular object based on: a first injury weight—corresponding to presence of the packaging obstructing the sharp surface of the particular object; and the first distance from the particular object to the surgical staff member at the first time.

In this example, the computer system can later access a second image of the surgical space recorded at a second time and detect a second set of features in the second image. Based on the second set of features, the computer system can: identify the particular object; detect absence of packaging obstructing the sharp surface of the particular object; and identify the surgical staff member. Accordingly, the computer system can calculate a second contamination risk of the particular object based on: a second contamination weight corresponding to absence of packaging obstructing the sharp surface of the particular object and greater than the first contamination weight; the staff contamination score of a second surface of the surgical staff member nearest and facing the particular object at approximately the second time; and a second distance from the particular object to the surgical staff member at approximately the second time. Concurrently, the computer system can calculate a second injury risk of the particular object based on: a second injury weight corresponding to absence of packaging obstructing the sharp surface of the particular object; and the second distance from the particular object to the surgical staff member at the second time.

8.3 Retention History

Similarly, the computer system can weight the injury risk of the particular object for the current time interval based on an injury history of objects of this type. For example, the computer system can implement injury weights of: "0.9" for suture needles; "0.0000" for surgical sponges; "0.6" for knives; "0.01" for needle drivers; and "0.1" for bone saws based on historical frequencies that objects of these types injured surgical staff during past surgeries. The computer system can thus identify a type of a particular object depicted in the current image and then weight the retention risk for this particular object for the current time interval accordingly.

8.4 Injury Score

The computer system can execute the foregoing process to calculate an injury risk component for the particular object and each surgical staff member detected in the current image. The computer system can then sum or otherwise combine these injury risk components to calculate an injury risk for the particular object for the current time interval.

As described above, the computer system can sum, integrate, or otherwise combine injury risks calculated for the particular object since start of the surgery to calculate an injury score for the particular object. For example, the computer system can calculate a weighted average of injury risks of the particular object thus derived from a sequence of images—such as recorded since the beginning of the surgery or over the last minute of the surgery—with greatest weight applied to the most-recent injury risk. In this example, the injury score can thus represent a rate of change of injury risk for the particular object; accordingly, the computer system can prompt surgical staff to consider or modify handling of the particular object if the injury score of the particular object is high or exceeds a threshold.

In another example, the computer system: calculates an injury score of the particular object based on an integral of its injury risks since the start of the surgery; calculates a derivative of the injury score to estimate a rate of change of risk that the particular object injures a surgical staff member; and prompts surgical staff to consider or modify handling of the particular object if this rate of change of risk exceeds a positive threshold rate of change.

Therefore, in this variation, the computer system can combine injury risks of a particular object over time into an injury score that represents a trajectory of injury risk of the particular object to all surgical staff in the surgical space since the start of the surgery.

9. Variation: Staff Injury Risk

In one variation shown in FIG. 2A, the computer system aggregates injury risk components between a particular surgical staff member and many objects (e.g., all known sharp objects) in the surgical space into one staff injury risk for this particular surgical staff member.

More specifically, the computer system can implement methods and techniques described above to calculate: a first injury risk component representing risk that a first sharp object in the surgical space has injured a particular surgical staff member during the current time interval; a second injury risk component representing risk that a second sharp object in the surgical space has injured the particular surgical staff member during the current time interval; a third injury risk component representing risk that a third sharp object in the surgical space has injured the particular surgical staff member during the current time interval; etc. for each sharp object detected in the current image of the surgical space. The computer system can then sum or otherwise combine these first, second, third, and other injury risk components for these sharp objects and the particular surgical staff member into a staff injury risk for the particular surgical staff member for the current time interval. This staff injury risk may thus represent a probability that the particular surgical staff member is injured (e.g., pricked, cut, scratched) by at least one sharp object in the surgical space during the current time interval. The computer system can then serve a prompt to the surgical space—such as directly to the particular surgical staff member or to a supervisor (e.g., a primary surgeon) in the surgical space—if the staff injury risk for the particular surgical staff member exceeds a threshold risk, such as to prompt the particular surgical staff member to address safe handling of sharp objects or to prompt investigation into possible injury to the particular surgical staff member.

Furthermore, the computer system can implement methods and techniques described above to sum, integrate, or otherwise combine staff injury risks for the particular surgical staff member since the start of the surgery in order to calculate a staff injury score for the particular surgical staff member, which may represent a probability that the particular surgical staff member was injured at some time since the start of the surgery.

Therefore, the computer system can calculate an injury risk of a particular object, which represents a probability that the particular object has injured any surgical staff member in the surgical space during the current time interval. If this injury risk exceeds a threshold risk, the computer system can thus prompt surgical staff to address this particular object, such as by increasing attentiveness to the particular object; or repositioning the particular object relative to a nearest surgical staff member. The computer system can also calculate an injury score of the particular object, which represents a probability that the particular object has injured any surgical staff member in the surgical space since the beginning of the surgery. If this injury risk exceeds a threshold score, the computer system can thus prompt surgical staff to address this particular object, such as by removing the particular object from the surgical space or initiating real-time retraining for handling objects of this type.

Furthermore, the computer system can aggregate injury risks across many sharp objects in the surgical space into a staff injury risk and staff injury score for one surgical staff member, which represents a probability that the particular surgical staff member was injured (e.g., stuck by a needle, cut by a knife or blade) during the current time interval and since the beginning of the surgery, respectively. When the staff injury score of the surgical staff member exceeds a threshold score, the computer system can thus: prompt the surgical staff member to confirm no injury; prompt the surgical staff member to immediately exit the surgical space for investigation of possible injury; and/or flag this surgical staff member for review following conclusion of the surgery.

10. Retention Risk

Figure 3:
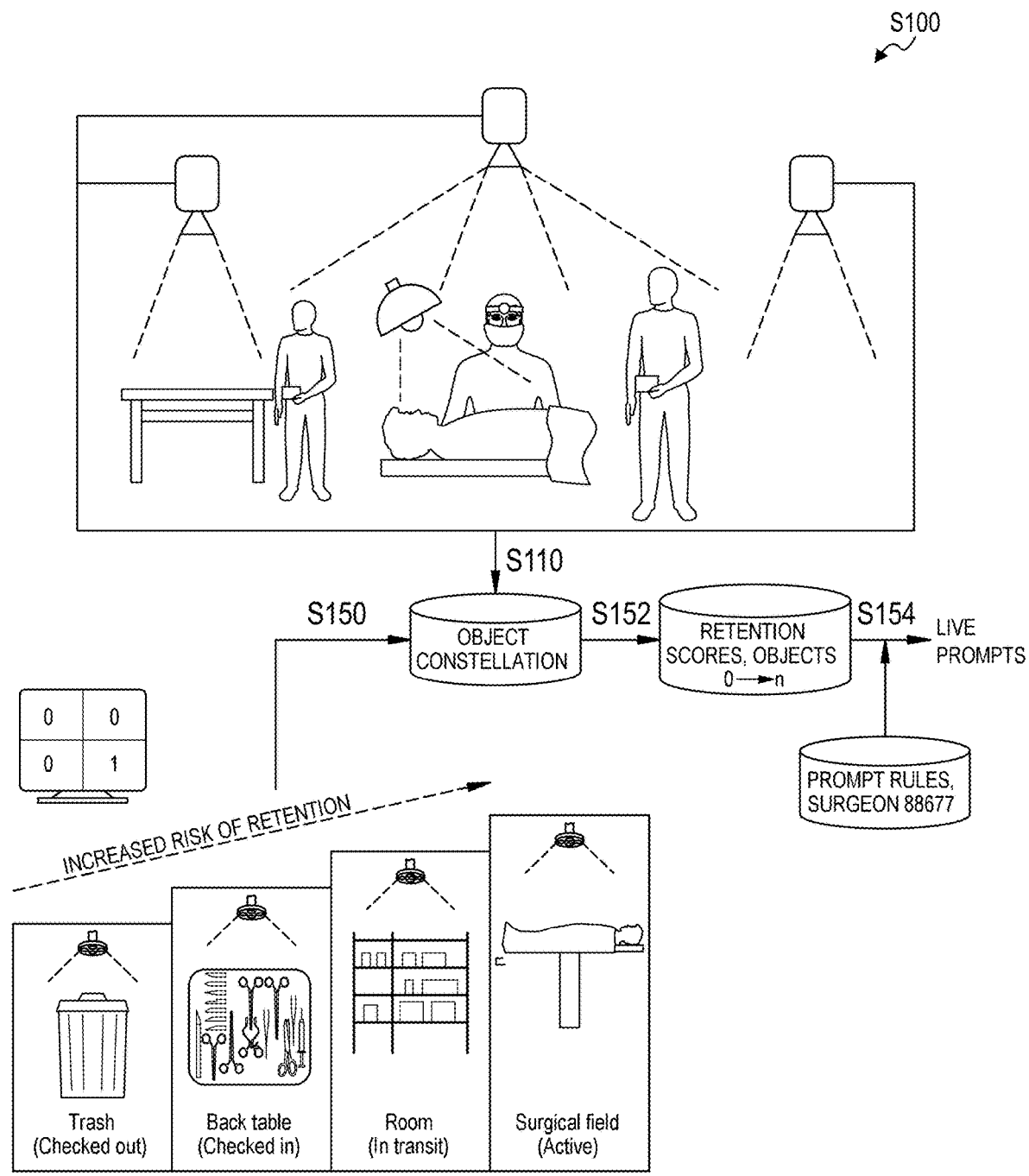
FIG. 3 is a flowchart representation of one variation of the method.

One variation of the method S100 shown in FIGS. 2A, 2B, and 3 includes Block S150, which recites calculating a first retention risk of the first object inversely proportional to the first distance. Generally, in Block S150, the computer system can calculate a probability that an object in the surgical space is unintentionally left in the patient's wound or surgical cavity upon conclusion of the surgery based on proximity of the object to the patient depicted in the current image and store this probably as a retention risk for this object for the current time interval.

In one implementation, the computer system implements methods and techniques similar to those described above to: detect a particular object (e.g., of a type commonly inserted into or placed in contact with a patient, such as a lap sponge, a suture needle, a knife)—in the current image; define retention risk zones around the particular object; detect the patient in the surgical space; detect the surgical cavity (or wound) on the patient; estimate a distance between the surgical cavity and the particular object; identify a particular retention risk zone around the particular object currently occupied by a nearest section of the surgical cavity; calculate a product (or other combination) of this distance and a retention risk weight for the particular retention risk zone; and store this product as a retention risk for the particular object for the current time interval. The computer system can also repeat this process for each other surgical cavity or wound detected on the patient in the current image and merge the resulting retention risk values into one retention risk for the particular object.

In a similar implementation, the computer system can: detect a wound on the patient depicted in a first image of the surgical space recorded at a first time; detect separation between the particular object and the wound on the patient at a first time; and calculate a first retention risk of the particular object inversely proportional to a first distance between the particular object and the wound and weighted by a first retention weight corresponding to separation between the particular object and the patient at the first time. Later, the computer system can: detect the wound on the patient depicted in a second image of the surgical space recorded at a second time; detect contact between the particular object and the wound on the patient at the second time; and then calculate a second retention risk of the particular object inversely proportional to a second distance between the particular object and the wound and weighted by a second retention weight, wherein the second retention weight is greater than the first retention weight and corresponds to contact between the particular object and the wound on the patient.

However, the computer system can implement a parametric function, a table, a model, or a statistic in any other form or format to calculate a retention risk for the particular object for the current time interval.

10.1 Driver Condition

In this variation, the computer system can also weight a retention risk of the particular object according to a driver condition of the particular object. For example, a knife blade installed on a knife handle, a suture needle stored in a needle tray or retained by a needle driver, and a surgical sponge retained by forceps may represent little or no retention risk to the patient; whereas a loose knife blade, loose suture needle, and loose surgical sponge may represent greater retention risk to the patient. Therefore, the computer system can implement methods and techniques described above to detect the driver condition of an object and to weight a retention risk according to the driver condition of the particular object, including: implementing a lower retention risk weight for the particular object if a driver is detected immediately adjacent the particular object; and implement-ing a higher retention risk weight for the particular object no such driver is detected immediately adjacent the particular object, as shown in FIG. 2B.

10.2 Object Size

Similarly, the computer system can weight the retention risk of the particular object for the current time interval based on a size of the particular object. For example, the computer system can implement retention weights of: "0.5" for suture needles; "0.2" for surgical sponges; "0.3" for disposable knife blades; "0.05" for needle drivers; and "0.001" for bone saws. The computer system can thus identify a type of a particular object depicted in the current image and then weight the retention risk for this particular object for the current time interval accordingly. Alternatively, the computer system can extract a size of the particular object from the image and calculate a retention weight for the object accordingly.

10.3 Retention History

Similarly, the computer system can weight the retention risk of the particular object for the current time interval based on a retention history of objects of this type. For example, the computer system can implement retention weights of: "0.7" for suture needles; "0.9" for surgical sponges; "0.1" for disposable knife blades; "0.005" for needle drivers; and "0.000" for bone saws based on historical frequencies that objects of these types were unintentionally left inside of patients. The computer system can thus identify a type of a particular object depicted in the current image and then weight the retention risk for this particular object for the current time interval accordingly.

10.4 Retention Score

This variation of the method S100 further includes Block S132, which recites calculating a retention score of the first object based on a combination of retention risks of the first object over time during the surgery. Generally, in Block S152, the computer system can sum, integrate, or otherwise combine the retention risks thus calculated for a particular object during the current and preceding time intervals into one numerical representation of the probability that the particular object will be retained in the patient upon conclusion of the surgery (i.e., a "retention score").

In one implementation, the computer system calculates a weighted average of retention risks of the particular object thus derived from a sequence of images—such as recorded since the beginning of the surgery or over the last minute of the surgery—with greatest weight applied to the most-recent retention risk and stores this weighted average at a retention score of the particular object. For example, the computer system can calculate a low retention risk for the particular object during a first time interval if the particular object is located far from the patient or on the floor of the surgical space; and the retention score of the particular object remains low or null accordingly. Later, as the particular object approaches the patient, the computer system can calculate greater retention risks for the particular object; and the retention score of the particular object thus increases accordingly. Furthermore, as the particular object makes contact with the patient, the computer system can calculate an even greater retention risk for the particular object; and the retention score of the particular object also increases at an increasing rate. Furthermore, as the particular object remains in with the patient, the computer system can calculate similar retention risks for the particular object; but the retention score of the particular object continues to increase, which indicates a current trajectory of the particular object to remain in contact with the patient. When the particular object is later removed from the patient, the computer system can calculate reduced retention risks for the particular object; and the retention score of the particular object drops or increases at a lesser rate, which indicates a current trajectory of removal of the particular object from the patient. However, if the particular object is not removed from the patient, the retention score for this object continues to increase; then, in response to the retention score for the particular object exceeding a threshold score, the computer system can serve a prompt to the surgical space—or to a primary surgeon or nearby assistant in the surgical space specifically—to retrieve the particular object, as described below.

10.5 Implantable Objects

Furthermore, some objects in the surgical space may be intended for retention in the patient, such as implants, sutures, and hernia meshes. Therefore, the computer system can detect and identify implantable objects in images of the surgical space and either: deactivate retention risk and retention score calculations for these implantable objects; or disable notifications related to retention of such implantable objects to the surgical space. Alternatively, the computer system can flag a particular object associated with a a retention score that exceeds a threshold score and serve a prompt to remove the particular object from the patient to the surgical space accordingly; the computer system can then disable all future prompts related to retention of this particular object responsive to a command or confirmation from a surgical staff member.

11. Variation: Patient Recall Score

In one variation shown in FIG. 2A, the computer system implements methods and techniques similar to those described above to generate and maintain one patient recall score that represents a probability that the patient will exit the surgical space with at least one unintentionally-retained object. In one implementation, the computer system sums, integrates, or otherwise combines all retention risks for all objects (or select objects of interest) in the surgical space since the start of the surgery and stores this over duration of the surgery and stores this combination as a patient recall score for the patient.

Therefore, the computer system can calculate a retention score of a particular object, which represents a current probability that the particular object will be retained in the patient upon conclusion of the surgery. When this retention score exceeds a threshold score, the computer system can prompt surgical staff to address this particular object, such as by: retrieving the particular object from the patient; confirming that the particular object has been intentionally left in contact with the patient (which may trigger the computer system to reduce or reset the retention score for the particular object); or confirming that the particular object is implantable. Concurrently, the computer system can calculate a patient recall score for the patient, which represents a probability that the patient will leave the surgical space with an unintentionally-retained object and/or be recalled to surgery to remove an unintentionally-retained object. When the patient recall score exceeds a threshold score, the computer system can thus serve a prompt to the surgical space to pause the surgery, scan the patient for unintentionally-retained objects (e.g., visually, with an x-ray scanner, or with a metal detector), and retrieve these objects accordingly. Alternatively, the computer system can render the patient recall score on a display in the surgical space; prior to closing the patient's surgical cavity or wound, surgical staff member may review this patient recall score and adjust time or effort spent searching the surgical cavity for retained objects based on this patient recall score.

12. Risk Labels

The computer system can execute the foregoing methods and techniques concurrently to calculate contamination risks, injury risks, and retention risks for each inanimate object (or for inanimate objects of interest, such as graspers, clamps, needle drivers, retractors, distractors, cutters, suction tips, microscopes) detected in a current image of the surgical space. The computer system can also update contamination scores, injury scores, and retention scores for each of these inanimate objects based on contamination, injury, and retention risks of these individual objects. The computer system can also label each object represented in an object constellation—derived from an image of the surgical space—with its contamination, injury, and retention risks and scores.

The computer system can similarly execute the foregoing methods and techniques concurrently to calculate and update patient infection scores and patient recall scores for the patient and can label an object representing the patient accordingly in each object constellation.

Similarly, the computer system can concurrently calculate and update staff injury risks and staff injury scores for each surgical staff member in the surgical space and can label objects representing these surgical staff accordingly in each object constellation.

Therefore, the computer system can label objects represented in an object constellation—representing one time interval during the surgery—with risk and score values in addition to types, orientations, and velocities of these objects. The computer system can also store this time-stamped object constellation in a surgery file or database affiliated with this surgery. (Alternatively, rather than generate an object constellation based on objects detected in the current image, the computer system can instead annotate the current image with types, packaging states, states, velocities, and/or risk values directly and store this annotated image in the surgery file or database affiliated with this surgery.) The computer system can then repeat this process for each subsequent image recorded during the surgery.

11. Surgical Space Map

Throughout the surgery, the computer system can interface with a display located in the surgical space to present a map of locations, orientations, risks, and/or scores of tracked objects present in the surgical space, as shown in FIG. 2A.

In one implementation, the computer system overlays object markers on a virtual map of the surgical space at locations of these objects detected in a current image of the surgical space and then renders this annotated surgical space map on the display. For example, the computer system can incorporate colored rings corresponding to contamination, injury, and retention around an object marker and adjust the opacity or color intensity of these colored rings according to the current contamination, injury, and retention risks (or scores), respectively, of the corresponding object. In another example, the computer system can: identify a first object associated with a current contamination score exceeding a threshold score (described below); render a first object marker for the first object in red on the virtual map; identify a second object associated with a current injury risk exceeding a threshold risk; render a second object marker for the second object in yellow on the virtual map; identify a third object associated with a current retention score exceeding a threshold score; and render a third object marker for the third object in purple on the virtual map. In this example, the computer system can also animate these object markers, such as by flashing or pulsing these object markers over the virtual map of the surgical space in order to draw attention of surgical staff and prompt correction of handling of specific objects within the surgical space. In yet another example, the computer system can render caption boxes—containing contamination, injury, and retention risks and scores—pointing to corresponding object markers on the display.

The computer system can similarly: annotate representations of the patient and surgical staff in the virtual map of the surgical space with patient infection scores, patient recall scores, staff injury risks, and/or staff injury scores corresponding to the patient and these surgical staff; and/or animate patient and surgical staff' markers when corresponding risks or scores exceed corresponding threshold values in order to draw attention of surgical staff and prompt correction of general object handling within the surgical space.

Alternatively, the computer system can: render a gradient of contamination scores of objects distributed throughout the surgical space over the virtual map; then render a gradient of injury risks of objects distributed throughout the surgical space over the virtual map; and then render a gradient of retention risks (or retention scores) for objects distributed throughout the surgical space over the virtual map; and regularly cycle through this sequence of gradient overlays, such as on a five-second interval. The computer system can similarly highlight regions of the virtual map depicting to regions of the surgical space containing objects associated with contamination, injury, and/or retention risks (or scores) that exceed corresponding threshold values.

In the foregoing implementations, the computer system can alternatively annotate a current image of the surgical space with object markers or gradients, etc. and render this annotated image on the display.

Therefore, the computer system can interface with a display located within the surgical space to enable surgical staff to quickly visualize locations of objects and their states within the surgical space. However, the computer system can interface with a heads-up display, augmented reality headset, projector, or other display system located within the surgical space or worn by surgical staff member to communicate a visual representation of objects and their states within the surgical space.

12. Notifications

Block S134 of the method S100 recites serving a prompt within the surgical space to address sterility of the first object in response to the first contamination score of the first object exceeding a threshold contamination score prior to contact between the first object and a patient occupying the surgical space. Similarly, Block S144 of the method S100 recites directing a prompt to the first surgical staff member to address the second injury risk of the first object in response to the second injury risk exceeding the first injury risk and exceeding a threshold injury warning risk. Furthermore, Block S154 of the method S100 recites, in response to the retention score of the first object exceeding a threshold retention score and in response to the third distance exceeding the fourth distance, serving a prompt to the second surgical staff member to retrieve the first object from the patient. Generally, in Blocks S134, S144, and S154, the computer system can serve prompts to preemptively address increases in contamination, injury, and/or retention risks or scores, respectively, for objects in the surgical space—such as prior to a contaminated object contacting the patient or entering the sterile field, prior to an object injuring (e.g., sticking, cutting) a surgical staff member, or prior to closure of the surgical cavity with an unintentionally-retained object.

12.1 Notification Intervention Rules

In one implementation shown in FIGS. 1, 3, and 4, the computer system implements generic, preset contamination, injury, and retention thresholds for triggering generation of prompts during the surgery. Alternatively, the computer system can access and implement contamination, injury, and retention thresholds predefined for a hospital group, hospital, or clinic hosting the surgery. In these implementations, the computer system can also: access a database of contamination, injury, and retention threshold groups defined for different surgery types; retrieve a contamination, injury, and retention threshold group for a type of the current surgery; and implement this contamination, injury, and retention threshold group to generate prompts during this surgery.

Yet alternatively, the computer system can access and implement contamination, injury, and retention thresholds defined for the surgery specifically, such as by the primary surgeon based on personal preferences or based on a difficulty of the surgery predicted by the surgeon.

However, the computer system can access and implement any other contamination, injury, and retention thresholds defined in any other way and by any other entity.

12.2 Passive Notifications

In one implementation, the computer system renders a list of types and locations of objects—detected in a current image of the space—ranked or filtered by contamination, injury, and/or retention risks or values. For example, the computer system can render textual descriptions of types and locations in the surgical space for: ten objects associated with the greatest contamination scores and currently in motion within two meters of the sterile field; five objects currently associated with greatest injury risks; and all objects associated with retention scores exceeding a threshold retention score. Additionally or alternatively, in this example, the computer system can annotate the virtual map of the surgical space described above with locations of these objects.

However, the computer system can implement any other method or technique to passively communicate locations of objects exhibiting greatest or significant contamination, injury, and retention risk in the surgical space.

12.3 Active Global Notifications

The computer system can also actively push prompts to surgical staff during the surgery based on contamination, injury, and retention risks and/or scores of objects moving through the surgical space.

In one example, in response to the patient infection score exceeding a threshold score, the computer system activates an alarm audible to all surgical staff in the surgical space and renders a textual prompt on the display in the surgical space to: improve handling of objects to reduce contamination; initiate real-time inter-operative retraining on sterile object handling; initiate rescrubbing and/or re-gloving for all surgical staff in the sterile field; and/or initiate re-sterilization of the sterile field or the surgical space more generally.

12.4 Targeted Notifications

The computer system can additionally or alternatively target prompts to individual surgical staff.

In one implementation, the computer system can serve a targeted notification to a particular surgical staff member by: transmitting a haptic trigger to a mobile device worn or carried by the particular surgical staff member; and concurrently rendering a visual notification (e.g., to discard a particular object with a high contamination score) on the display arranged in the surgical space remotely from the patient. For example, surgical staff can each wear or carry a local device on a wrist, hung from a neck, or clipped to a waistband. Upon receipt of a haptic trigger from the computer system (e.g., via a local gateway or wireless router), a local device can activate a vibrator in order to haptically indicate to the corresponding surgical staff member that a visual notification targeted to the surgical staff member is pending on the display. The computer system can concurrently generate a visual prompt paired with the haptic trigger, such as including: a name or other identification of the surgical staff member; a text string describing the prompt; a textual description of a corresponding object (e.g., "lap sponge," "suture needle"); a graphic representation of the corresponding object; and/or a region of the current image of the surgical space depicting the corresponding object; etc. The computer system can serve this visual prompt to the display, which can render this visual prompt concurrently with vibration of the local device. The surgical staff member may therefore look toward the display after perceiving vibration of her local device in order to access the textual description and related content for an action (e.g., discarding a particular object) thus recommended by the computer system.

The computer system can additionally or alternatively serve targeted audible alarms—corresponding to visual prompts rendered on the display—to headsets, earpieces, or headphones worn by surgical staff. The system can similarly serve targeted audible prompts—such as including audible descriptions of an action, a target object of the action, and a location of the target object—to headsets worn by surgical staff. Additionally or alternatively, the computer system can serve: targeted visual content to augmented reality headsets, heads-up or eyes-up displays, or smartwatches worn by surgical staff.

However, the computer system can implement any other method or technique and can interface with any other general or personal devices in the surgical space to serve targeted prompts to individual surgical staff (or sub-groups of surgical staff) in the surgical staff.

12.5 Examples: Contamination Notification

For example, in response to a contamination score of a particular object in the surgical space exceeding a threshold contamination score and if this particular object is disposable (e.g., lap sponge, a suture needle), the computer system can: identify a particular surgical staff member currently handling or otherwise nearest the particular object; and target a notification to discard the particular object directly to this particular surgical staff member.

In a similar example shown in FIG. 2B, the computer system can detect or calculate a sterile field around the patient in the current image (e.g., a boundary extending one-meter beyond the patient). Then, if the current location of the particular object at the current time falls outside of the sterile field, the computer system can direct a prompt to discard the particular object to a circulatory staff member in the surgical space. However, if the current location of the particular object at the current time falls within the sterile field, the computer system can direct this prompt—to discard the particular object and then re-glove—to a sterile staff member within the sterile field.

Alternatively, in response to a contamination score of a particular object in the surgical space exceeding a threshold contamination score and if this particular object is not disposable (e.g., a microscope), the computer system can: identify a particular surgical staff member currently handling or otherwise nearest the particular object; and target a notification to drape or sterilize the particular object or to remove the particular object from the surgical space directly to this particular surgical staff member.

12.6 Example: Injury Notification

In another example shown in FIG. 2B, in response to an injury risk of a particular object in the surgical space exceeding a threshold injury risk, the computer system can: identify a particular surgical staff member currently handling or otherwise nearest the particular object; and target a notification to correct handling of the particular object—in order to reduce risk of injury—directly to this particular surgical staff member.

The computer system can also selectively escalate prompts related to possible injury by an object in the surgical space. For example, if a current injury risk of a particular object has increased from preceding injury risks and now exceeds a threshold injury warning risk, the computer system can direct a prompt to improve handling of the particular object to a particular surgical staff member currently handling or nearest the particular object. However, if the injury risk of the particular object continues to increase and then exceeds a threshold injury investigation risk greater than the threshold injury warning risk, the computer system can serve a second prompt within the surgical space, such as to surgical staff generally, to a supervisor, or to the primary surgeon to prompt investigation into whether the particular object injured the particular surgical staff member.

12.7 Example: Retention Notification

In yet another example shown in FIG. 2B, in response to a retention score of a particular object in the surgical space exceeding a threshold retention score, the computer system can target a notification to retrieve the particular object—including a description of the particular object—from the patient to the primary surgeon and to the surgical assistant.

12.8 Example: Staff Injury Notification

In another example shown in FIG. 2A, in response to a staff injury score of a particular surgical staff member in the surgical space exceeding a threshold staff injury score, the computer system can: target a notification to the particular surgical staff member to confirm absence of injury; and/or target a notification to a supervisor in the surgical space (e.g., the primary surgeon, the surgical assistant) to verify absence of injury to the particular surgical staff member.

13. Object Disposal and Removal

Furthermore, the computer system can detect disposal of a particular object, such as into a disposal container based on proximity of the particular object and the disposal container. Similarly, the computer system can detect removal of the particular object from the surgical space, such as by tracking exit of the particular object via a doorway of the surgical space. Once the computer system detects disposal or removal of the particular object, the computer system can disable contamination, injury, and retention tracking for this object and remove the particular object from calculations of subsequent contamination, injury, and retention risks and scores for other objects in the surgical space.

14. Post-Operative Guidance

In one variation, the computer system derives post-operative insights from object constellations and inter-operative object flow through the surgical space during the surgery. For example, the computer system can score efficiency and complexity of the surgery, sterility management of objects during the surgery, consumption of objects, and/or injury related to object flow during the surgery, etc. based on these object constellations. For example, such scores thus derived by the computer system may represent benchmarking metrics for cases, surgeons, hospitals, and/or hospital systems, etc.

In one implementation, the computer system calculates spatial and temporal variance of paths of individual objects consumed during the surgery and calculates an average retention time from removal of objects from inventory (e.g., from a object tray, from the back table) to use of these objects at the patient (or to disposal of these objects) (i.e., "retention time"). The computer system can then quantify an efficiency of the surgery: inversely proportional to these spatial and temporal variances; and/or inversely proportional to the average retention time. The computer system can also quantify a complexity of the surgery, such as: proportional to a total quantity of objects consumed; proportional to a ratio of total objects used at the patient to total quantity of objects consumed; and/or proportional to variance in location of initial contact between objects and the patient (which may be a measure of a size of a wound) during the surgery. The computer system can also quantify an efficacy of the surgical staff, such as inversely proportional to: aggregate or average staff injury scores for all surgical staff upon conclusion of the surgery; the final patient infection score upon conclusion of the surgery; a ratio of total consumed objects to a quantity of objects brought into inventory; and/or aggregate or average final contamination scores for all objects that entered the surgical space in sterile conditions. In this implementation, the computer system can also flag this surgery or this surgical staff for post-operative review: if these efficiency, complexity, and efficacy metrics for this surgery and surgical staff deviate significantly from historical metrics for similar surgeries or surgical staff; if the aggregate or average staff injury scores for these surgical staff exceeds a threshold; or if the final patient infection score upon conclusion of the surgery exceeds a threshold. Accordingly, a reviewer may access and review an image feed and/or a timeseries of object constellations recorded during the surgery in order to verify or validate procedures of surgical staff during the surgery.

The computer system can also flag periods of the surgery in which a subset of objects within the surgical space traversed anomalous paths—for their object types—through the surgical space and then prompt a reviewer to specifically review these periods of the surgery. The computer system can then selectively serve clips of the image feed and/or sequences of object constellations corresponding to these flagged periods during the surgery to a reviewer portal to enable the reviewer to quickly access and review periods of the surgery most likely to depict errors or opportunities to improve surgical efficiency.

In another implementation, the computer system selectively prompts post-operative assessment of the patient at a frequency or scale based on efficiency, complexity, and/or efficacy of the surgery or surgical staff. For example, the computer system can prompt hospital staff to plan a post-operative hospital stay for the patient and/or schedule follow-up frequency for the patient proportional to surgery complexity and inversely proportional to surgery efficiency and surgical staff efficacy.

In another example, the computer system can prompt hospital staff to initiate a post-operative antibiotic regimen for the patient based on the patient infection score or based on aggregate contamination scores of objects consumed during the surgery. In a similar example, the computer system can generate a recommendation for supplemental post-operative administration of antibiotics to the patient proportional to the patient infection score upon conclusion of the surgery.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for tracking objects within a surgical space during a surgery comprising:
   based on a first image depicting the surgical space at a first time:
      detecting a first constellation of objects in the surgical space at the first time;
      estimating distances from each object, in a first subset of objects in the first constellation of objects, to a first object in the first constellation of objects at the first time; and
      calculating a first contamination risk of the first object based on contamination scores and distances to the first object for each object in the first subset of objects at the first time;
   based on a second image depicting the surgical space at a second time succeeding the first time:
      detecting a second constellation of objects in the surgical space at the second time;
      estimating distances from each object, in a second subset of objects in the second constellation of objects, to the first object at the second time; and
      calculating a second contamination risk of the first object based on contamination scores and distances to the first object for each object in the second subset of objects at the second time;
   calculating a first contamination score of the first object based on a combination of the first contamination risk and the second contamination risk; and
   in response to the first contamination score of the first object exceeding a threshold contamination score prior to contact between the first object and a patient occupying the surgical space rendering a visual prompt, on a display arranged within the surgical space, to address sterility of the first object.

2. The method of claim 1:
further comprising:
  accessing a first set of color frames recorded by a set of color cameras arranged in the surgical space at approximately the first time; and
  compiling the first set of color frames into the first image defining a first 3D color point cloud based on known locations of the set of color cameras;
wherein detecting the first constellation of objects in the first image comprises, for each object in the first set of objects:
  detecting a type of the object; and
  extracting a lateral location, a longitudinal location, and a depth location of the object in the surgical space from the first image; and
wherein estimating distances from each object, in a first subset of objects in the first constellation of objects, to the first object comprises, for each object in the first subset of objects:
  calculating a distance from the lateral location, the longitudinal location, and the depth location of the object to a first lateral location, a first longitudinal location, and a first depth location of the first object at the first time.

3. The method of claim 1:
wherein detecting the first constellation of objects in the surgical space comprises detecting the first object, a retractor, a surgical towel, a scrubbed surgical staff member, a nonsterile surgical staff member, and the patient depicted in the first image;
wherein calculating the first contamination risk of the first object comprises:
  calculating a first combination of a retractor contamination score of the retractor at approximately the first time and a first distance between the first object and the retractor;
  calculating a second combination of a towel contamination score of the surgical towel at approximately the first time and a second distance between the first object and the surgical towel;
  calculating a third combination of a scrubbed staff contamination score of the scrubbed surgical staff member at approximately the first time and a third distance between the first object and the scrubbed surgical staff member;
  calculating a fourth combination of a nonsterile staff contamination score of the nonsterile surgical staff member at approximately the first time and a fourth distance between the first object and the surgical staff member; and
  calculating the first contamination risk based on the first combination, the second combination, the third combination, and the fourth combination; and
wherein rendering the visual prompt to address sterility of the first object comprises rendering the visual prompt to address sterility of the first object prior to a sixth distance between the first object and the patient falling below a threshold sterile field distance.

4. The method of claim 1:
wherein detecting the first constellation of objects in the surgical space at the first time based on the first image comprises detecting a second object in contact with a floor of the surgical space depicted in the first image;
further comprising, in response to detecting the second object in contact with the floor of the surgical space, updating a second contamination score of the second object to reflect confirmed contamination of the second object;
wherein detecting the second constellation of objects in the surgical space at the second time comprises detecting the first object and the second object in the second image; and
wherein calculating the second contamination risk of the first object comprises calculating the second contamination risk of the first object proportional to the second contamination score of the second object and inversely proportional to a second distance between the first object and the second object depicted in the second image.

5. The method of claim 1:
wherein detecting the second constellation of objects in the surgical space at the second time based on the second image comprises:
  detecting the first object at a first location in the second image; and
  detecting a sterile field around the patient in the second image; and
wherein rendering the visual prompt to address sterility of the first object comprises:
  in response to the first location of the first object at the second time falling outside of the sterile field, directing the prompt to a circulatory staff member in the surgical space; and
  in response to the first location of the first object at the second time falling within the sterile field, directing the prompt to a sterile staff member within the sterile field.

6. The method of claim 1:
wherein detecting the second constellation of objects in the surgical space at the second time based on the second image comprises detecting the first object, a first surgical staff member, and a second surgical staff member in the second image; and
wherein rendering the visual prompt to address sterility of the first object comprises, in response to a first distance between the first object and the first surgical staff member exceeding a second distance between the first object and the second surgical staff member, directing the visual prompt to the second surgical staff member.

7. The method of claim 6, wherein directing the visual prompt to the second surgical staff member comprises:
  serving a haptic trigger to a mobile device worn by the second surgical staff member; and
  rendering a visual notification to discard the first object on a display arranged in the surgical space remotely from the patient, the visual notification identifying the second surgical staff member.

8. The method of claim 1, further comprising:
based on the first image, calculating a third contamination risk of a second object based on contamination scores and distances to the first object for each object in a second subset of objects in the first constellation of objects at the first time;
based on the second image:
  calculating a fourth contamination risk of the second object based on contamination scores and distances to the second object for each object in a third subset of objects at the second time;
  detecting the first object in a first location of the surgical space at approximately the second time; and
  detecting the second object in a second location of the surgical space at approximately the second time;

calculating a second contamination score of the second object based on a second combination of the third contamination risk and the fourth contamination risk; and at approximately the second time:
rendering a virtual representation of the surgical space on a display arranged in the surgical space remotely from the patient;
rendering a first identifier of the first object over a first region of the virtual representation corresponding to the first location in the surgical space and annotated with the first contamination score on the display; and
rendering a second identifier of the second object over a second region of the virtual representation corresponding to the second location in the surgical space and annotated with the second contamination score on the display.

9. The method of claim 1:
based on the first image, calculating a third contamination risk of a second object based on contamination scores and distances to the first object for each object in a second subset of objects in the first constellation of objects at the first time;
based on the second image, calculating a fourth contamination risk of the second object based on contamination scores and distances to the second object for each object in a third subset of objects at the second time;
calculating a second contamination score of the second object based on a second combination of the third contamination risk and the fourth contamination risk;
calculating a patient infection risk based on a combination of the first contamination score for the first object and the second contamination score for the second object; and
designating supplemental antibiotic administration to the patient proportional to the patient infection risk.

10. The method of claim 1, further comprising accessing the threshold contamination score specified by a primary surgeon in the surgical space prior to the surgery.

11. The method of claim 1:
wherein detecting the first constellation of objects in the first image comprises:
detecting a first set of features in the first image;
identifying a second object comprising a back table located at a second location in the surgical space based on the first set of features;
identifying a third object comprising a needle tray occupying the back table based on the first set of features;
identifying the first object comprising a suture needle located at a first location in the surgical space and occupying the needle tray based on the first set of features; and
identifying a fourth object comprising a first nonsterile region of a first surgical staff member located at a fourth location in the surgical space based on the first set of features;
wherein calculating the first contamination risk of the first object comprises:
calculating a first product of:
a staff contamination score of the first surgical staff member at approximately the first time; and
a second distance from the first location to the fourth location in the surgical space; and weighting the first product by a first weight, corresponding to presence of the first object in the needle tray, to calculate the first contamination risk of the first object;
wherein detecting the second constellation of objects in the second image comprises:
detecting a second set of features in the first image;
identifying a fifth object comprising a needle driver located at a fifth location in the surgical space based on the second set of features; and
identifying the first object coupled to the fifth object based on the second set of features; and
wherein calculating the second contamination risk of the first object comprises:
accessing a driver contamination score of the needle driver at approximately the second time;
calculating a third product of:
the staff contamination score of the first surgical staff member at approximately the second time; and
a third distance from the fifth location to a sixth location in the surgical space; and
weighting a combination of the driver contamination score and the third product by a second weight to calculate the second contamination risk of the first object, the second weight greater than the first weight and corresponding to removal of the first object from the needle tray.

12. The method of claim 1:
wherein detecting the first constellation of objects in the first image comprises:
detecting a first set of features in the first image;
identifying the first object comprising a sharp surface based on the first set of features;
detecting presence of a packaging obstructing the sharp surface of the first object based on the first set of features; and
identifying a second object comprising a surgical staff member based on the first set of features;
wherein calculating the first contamination risk of the first object comprises calculating the first contamination risk of the first object based on a first contamination weight, a staff contamination score of a first surface of the surgical staff member facing the first object at approximately the first time, and a first distance from the first object to the surgical staff member at approximately the first time, the first contamination weight corresponding to presence of the packaging obstructing the sharp surface of the first object;
further comprising calculating a first injury risk of the first object based on a first injury weight and the first distance from the first object to the surgical staff member at the first time, the first injury weight corresponding to presence of the packaging obstructing the sharp surface of the first object;
wherein detecting the second constellation of objects in the second image comprises:
detecting a second set of features in the second image;
identifying the first object based on the second set of features;
detecting absence of packaging obstructing the sharp surface of the first object based on the second set of features; and
identifying the second object based on the second set of features;
wherein calculating the second contamination risk of the first object comprises calculating the second contamination risk of the first object based on a second contamination weight, the staff contamination score of a second surface of the surgical staff member facing the first object at approximately the second time, and a second distance from the first object to the surgical staff member at approximately the second time, the second contamination weight corresponding to absence of packaging obstructing the sharp surface of the first object and greater than the first contamination weight;

further comprising calculating a second injury risk of the first object based on a second injury weight and the second distance from the first object to the surgical staff member at the second time, the second injury weight corresponding to absence of packaging obstructing the sharp surface of the first object; and further comprising, in response to the second injury risk exceeding the first injury risk and exceeding a threshold injury warning risk, serving a second prompt within the surgical space to address the second injury risk of the first object.

13. The method of claim 1:
wherein detecting the first constellation of objects in the first image comprises:
  detecting a first set of features in the first image;
  identifying the first object comprising a surgical textile based on the first set of features;
  detecting presence of a packaging containing the first object based on the first set of features; and
  identifying a second object comprising the patient based on the first set of features;
wherein calculating the first contamination risk of the first object comprises calculating the first contamination risk of the first object based on a first contamination weight and contamination scores and distances to the first object for each object in the first subset of objects at the first time, the first contamination weight corresponding to presence of the packaging containing the first object;
further comprising calculating a first retention risk of the first object inversely proportional to a first distance from the first object to the patient at the first time;
wherein detecting the second constellation of objects in the second image comprises:
  detecting a second set of features in the first image;
  identifying the first object based on the second set of features;
  detecting absence of packaging containing the first object based on the second set of features; and
  identifying the second object based on the second set of features;
wherein calculating the second contamination risk of the first object comprises calculating the second contamination risk of the first object based on a second contamination weight and contamination scores and distances to the first object for each object in the second subset of objects at the second time, the second contamination weight corresponding to absence of packaging containing the first object and greater than the first contamination weight;
further comprising calculating a second retention risk of the first object inversely proportional to a second distance from the first object to the patient at the second time; and
further comprising:
  calculating a retention score of the first object based on an integral of retention risks of the first object over time during the surgery; and
  in response to the retention score of the first object exceeding a threshold retention score, serving a second prompt within the surgical space to retrieve the first object from the patient.

14. A method for tracking objects within a surgical space comprising:
based on a first image depicting the surgical space at a first time:
  detecting a first object and a set of surgical staff in the surgical space at the first time;
  detecting a first packaging condition of the first object at the first time;
  estimating distances from each surgical staff member, in the set of surgical staff, to the first object at the first time; and
  calculating a first injury risk of the first object based on the first packaging condition of the first object and inversely proportional to distances to the first object for each surgical staff member in the set of surgical staff at the first time;
based on a second image depicting the surgical space at a second time succeeding the first time:
  detecting the first object and the set of surgical staff in the surgical space at the second time;
  detecting a second packaging condition of the first object at the second time;
  estimating distances from each surgical staff member, in the set of surgical staff, to the first object at the second time;
  identifying a first surgical staff member, in the set of surgical staff, nearest the first object based on distances from each surgical staff member, in the set of surgical staff, to the first object at the second time; and
  calculating a second injury risk of the first object based on the second packaging condition of the first object and distances to the first object for each surgical staff member in the set of surgical staff at the second time; and
in response to the second injury risk exceeding the first injury risk and exceeding a threshold injury warning risk, rendering, on a display, a visual prompt to the first surgical staff member to address the second injury risk of the first object.

15. The method of claim 14:
further comprising, serving a haptic trigger to a mobile device worn by the first surgical staff member; and
wherein rendering the visual prompt to address the second injury risk comprises, in response to the second injury risk exceeding the first injury risk and exceeding the threshold injury warning risk, rendering a visual notification to discard the first object on the display arranged in the surgical space remotely from the patient.

16. The method of claim 14, further comprising:
based on a third image depicting the surgical space at a third time succeeding the second time:
  detecting the first object and the set of surgical staff in the surgical space at the second time;
  detecting the second packaging condition of the first object at the third time; and
  estimating distances from each surgical staff member, in the set of surgical staff, to the first object at the third time;
  identifying the first surgical staff member, in the set of surgical staff, nearest the first object based on distances from each surgical staff member, in the set of surgical staff, to the first object at the third time; and calculating a third injury risk of the first object based on the second packaging condition of the first object and distances to the first object for each surgical staff member in the set of surgical staff at the third time;

in response to the third injury risk exceeding the second injury risk and exceeding a threshold injury investigation risk, directing a prompt to a second surgical staff member, in the set of surgical staff, to investigate injury to the first surgical staff member by the first object.

17. The method of claim 14:
wherein detecting the first packaging condition of the first object at the first time comprises, based on the first image, detecting presence of a packaging obstructing a sharp surface of the first object;
wherein calculating the first injury risk of the first object comprises calculating the first injury risk of the first object based on a first combination of distances to the first object for each surgical staff member in the set of surgical staff at the first time and a first injury weight corresponding to presence of the packaging obstructing the sharp surface of the first object;
wherein detecting the second packaging condition of the first object at the second time comprises, based on the second image, detecting absence of packaging obstructing the sharp surface of the first object; and
wherein calculating the second injury risk of the first object comprises calculating the second injury risk of the first object based on a second combination of distances to the first object for each surgical staff member in the set of surgical staff at the second time and a second injury weight corresponding to absence of packaging obstructing the sharp surface of the first object, the second injury weight greater than the first injury weight.

18. The method of claim 14, further comprising:
based on the first image:
  detecting a first constellation of objects in the surgical space at the first time;
  estimating distances from each object, in the first constellation of objects, to the first object at the first time; and
  calculating a first contamination risk of the first object based on contamination scores and distances to the first object for each object in the first constellation of objects at the first time;
based on the second image:
  detecting a second constellation of objects in the surgical space at the second time;
  estimating distances from each object, in the second constellation of objects, to the first object at the second time; and
  calculating a second contamination risk of the first object based on contamination scores and distances to the first object for each object in the second constellation of objects at the second time;
calculating a first contamination score of the first object based on a combination of the first contamination risk and the second contamination risk; and
in response to the first contamination score of the first object exceeding a threshold contamination score prior to contact between the first object and a patient occupying the surgical space, serving a prompt within the surgical space to address sterility of the first object.

19. A method for tracking objects within a surgical space during a surgery comprising:

based on a first image depicting the surgical space at a first time:
  detecting a first object and a patient in the surgical space at the first time;
  estimating a first distance from the first object to the patient at the first time; and
  calculating a first retention risk of the first object inversely proportional to the first distance;
based on a second image depicting the surgical space at a second time succeeding the first time:
  detecting the first object, the patient, a first surgical staff member proximal the first object, and a second surgical staff member proximal the first object in the surgical space at the second time;
  estimating a second distance from the first object to the patient at the second time;
  estimating a third distance from the first object to the first surgical staff member at the second time;
  estimating a fourth distance from the first object to the second surgical staff member at the second time; and
  calculating a second retention risk of the first object inversely proportional to the second distance;
calculating a retention score of the first object based on a combination of retention risks of the first object over time during the surgery; and
in response to the retention score of the first object exceeding a threshold retention score and in response to the third distance exceeding the fourth distance:
  rendering, on a display arranged in the surgical space, a visual prompt directed to the second surgical staff member to retrieve the first object from the patient.

20. The method of claim 19:
wherein detecting the patient in the surgical space at the first time comprises detecting a wound on the patient depicted in the first image;
wherein estimating the first distance from the first object to the patient at the first time comprises detecting separation between the first object and the wound on the patient at the first time based on the first image;
wherein calculating the first retention risk of the first object comprises calculating the first retention risk of the first object inversely proportional to the first distance and weighted by a first retention weight corresponding to separation between the first object and the patient at the first time;
wherein detecting the patient in the surgical space at the second time comprises detecting the wound on the patient depicted in the second image;
wherein estimating the second distance from the first object to the patient at the second time comprises detecting contact between the first object and the wound on the patient at the second time based on the second image; and
wherein calculating the second retention risk of the first object comprises calculating the second retention risk of the first object inversely proportional to the second distance and weighted by a second retention weight, the second retention weight greater than the first retention weight and corresponding to contact between the first object and the wound on the patient at the second time.

21. A method for tracking objects within a surgical space during a surgery comprising:
accessing a first set of color frames recorded by a set of color cameras arranged in the surgical space at approximately a first time; and compiling the first set of color frames into a first image defining a first 3D color point cloud based on known locations of the set of color cameras;

based on the first image depicting the surgical space at the first time:

detecting a first constellation of objects in the surgical space at the first time by:

detecting a type of the object; and extracting a lateral location, a longitudinal location, and a depth location of the object in the surgical space from the first image;

estimating distances from each object, in a first subset of objects in the first constellation of objects, to a first object in the first constellation of objects at the first time by calculating a distance from the lateral location, the longitudinal location, and the depth location of the object to a first lateral location, a first longitudinal location, and a first depth location of the first object at the first time;

calculating a first contamination risk of the first object based on contamination scores and distances to the first object for each object in the first subset of objects at the first time;

based on a second image depicting the surgical space at a second time succeeding the first time:

detecting a second constellation of objects in the surgical space at the second time;

estimating distances from each object, in a second subset of objects in the second constellation of objects, to the first object at the second time; and calculating a second contamination risk of the first object based on contamination scores and distances to the first object for each object in the second subset of objects at the second time;

calculating a first contamination score of the first object based on a combination of the first contamination risk and the second contamination risk; and in response to the first contamination score of the first object exceeding a threshold contamination score prior to contact between the first object and a patient occupying the surgical space, serving a prompt, within the surgical space to address sterility of the first object.

22. A method for tracking objects within a surgical space during a surgery comprising:

based on a first image depicting the surgical space at a first time:

detecting a first constellation of objects in the surgical space at the first time;

estimating distances from each object, in a first subset of objects in the first constellation of objects, to a first object in the first constellation of objects at the first time;

calculating a first contamination risk of the first object based on contamination scores and distances to the first object for each object in the first subset of objects at the first time; and calculating a third contamination risk of a second object based on contamination scores and distances to the first object for each object in a second subset of objects in the first constellation of objects at the first time;

based on a second image depicting the surgical space at a second time succeeding the first time:

detecting a second constellation of objects in the surgical space at the second time;

estimating distances from each object, in a second subset of objects in the second constellation of objects, to the first object at the second time;

calculating a second contamination risk of the first object based on contamination scores and distances to the first object for each object in the second subset of objects at the second time;

calculating a fourth contamination risk of the second object based on contamination scores and distances to the second object for each object in a third subset of objects at the second time;

detecting the first object in a first location of the surgical space; and detecting the second object in a second location of the surgical space;

calculating a first contamination score of the first object based on a combination of the first contamination risk and the second contamination risk;

calculating a second contamination score of the second object based on a second combination of the third contamination risk and the fourth contamination risk; and at approximately the second time, in response to the first contamination score of the first object exceeding a threshold contamination score prior to contact between the first object and a patient occupying the surgical space:

rendering a virtual representation of the surgical space on a display arranged in the surgical space remotely from the patient to address sterility of the first object;

rendering a first identifier of the first object over a first region of the virtual representation corresponding to the first location in the surgical space and annotated with the first contamination score on the display; and rendering a second identifier of the second object over a second region of the virtual representation corresponding to the second location in the surgical space and annotated with the second contamination score on the display.

\* \* \* \* \*